United States Patent
Nguyen et al.

(10) Patent No.: US 11,278,577 B2
(45) Date of Patent: Mar. 22, 2022

(54) ENGINEERED BACTERIA SECRETING THERAPEUTIC PROTEINS AND METHODS OF USE THEREOF

(71) Applicant: President and Fellows of Harvard College, Cambridge, MA (US)

(72) Inventors: Peter Q. Nguyen, Malden, MA (US); Neel Satish Joshi, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 296 days.

(21) Appl. No.: 16/328,303

(22) PCT Filed: Aug. 31, 2017

(86) PCT No.: PCT/US2017/049639
§ 371 (c)(1),
(2) Date: Feb. 26, 2019

(87) PCT Pub. No.: WO2018/045184
PCT Pub. Date: Mar. 8, 2018

(65) Prior Publication Data
US 2019/0201457 A1    Jul. 4, 2019

Related U.S. Application Data

(60) Provisional application No. 62/381,961, filed on Aug. 31, 2016.

(51) Int. Cl.
| | | |
|---|---|---|
| *C12P 21/06* | (2006.01) |
| *A61K 35/74* | (2015.01) |
| *C07K 14/245* | (2006.01) |
| *C12P 21/02* | (2006.01) |
| *A61P 1/00* | (2006.01) |
| *A61K 9/00* | (2006.01) |
| *A61K 9/02* | (2006.01) |
| *A61K 9/20* | (2006.01) |
| *A61K 9/48* | (2006.01) |
| *C07K 19/00* | (2006.01) |

(52) U.S. Cl.
CPC ............ *A61K 35/74* (2013.01); *A61K 9/0031* (2013.01); *A61K 9/0056* (2013.01); *A61K 9/02* (2013.01); *A61K 9/20* (2013.01); *A61K 9/48* (2013.01); *A61P 1/00* (2018.01); *C07K 14/245* (2013.01); *C07K 19/00* (2013.01); *C12P 21/02* (2013.01); *C07K 2317/622* (2013.01); *C07K 2319/02* (2013.01); *C07K 2319/036* (2013.01); *C07K 2319/21* (2013.01)

(58) Field of Classification Search
CPC ...... A61K 39/00; A61K 39/02; A61K 39/395; A61K 49/00; A61K 35/74
USPC ....... 424/9.1, 9.2, 93.2, 130.1, 184.1, 185.1, 424/234.1, 235.1
See application file for complete search history.

(56) References Cited

U.S. PATENT DOCUMENTS

| 2012/0225453 A1 | 9/2012 | Withers, III et al. |
| 2015/0291991 A1 | 10/2015 | Hochschild et al. |

FOREIGN PATENT DOCUMENTS

| WO | 2015/097289 A1 | 7/2015 |
| WO | 2017/087827 A1 | 5/2017 |

OTHER PUBLICATIONS

International Search Report and Written Opinion for Application No. PCT/US2017/049639, dated Jan. 2, 2018, 9 pages.
International Preliminary Report on Patentability for Application No. PCT/US2017/049639, dated Mar. 14, 2019, 7 pages.

*Primary Examiner* — Albert M Navarro
(74) *Attorney, Agent, or Firm* — Foley Hoag LLP

(57) ABSTRACT

Engineered bacteria that secrete therapeutic polypeptides, pharmaceutical compositions comprising the bacteria, methods for producing recombinant polypeptides, and methods for using the bacteria for diagnostic and therapeutic purposes are provided.

22 Claims, 12 Drawing Sheets
Specification includes a Sequence Listing.

```
SEQUENCE LISTING

<160> NUMBER OF SEQ ID NOS: 33

<210> SEQ ID NO 1
<211> LENGTH: 22
<212> TYPE: PRT
<213> ORGANISM: Escherichia coli

<400> SEQUENCE: 1

Gly Val Val Pro Gln Tyr Gly Gly Gly Asn His Gly Gly Gly
1               5                   10                  15

Asn Asn Ser Gly Pro Asn
            20

<210> SEQ ID NO 2
<211> LENGTH: 19
<212> TYPE: PRT
<213> ORGANISM: Escherichia coli

<400> SEQUENCE: 2

Met Lys Lys Ile Trp Leu Ala Leu Ala Gly Leu Val Leu Ala Phe Ser
1               5                   10                  15

Ala Ser Ala

<210> SEQ ID NO 3
<211> LENGTH: 23
<212> TYPE: PRT
<213> ORGANISM: Escherichia coli

<400> SEQUENCE: 3

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 4
<211> LENGTH: 21
<212> TYPE: PRT
<213> ORGANISM: Escherichia coli
```

-continued

<400> SEQUENCE: 4

Met Lys Gln Ala Leu Arg Val Ala Phe Gly Phe Leu Ile Leu Trp Ala
1               5                   10                  15

Ser Val Leu His Ala
            20

<210> SEQ ID NO 5
<211> LENGTH: 19
<212> TYPE: PRT
<213> ORGANISM: Escherichia coli

<400> SEQUENCE: 5

Met Arg Val Leu Leu Phe Leu Leu Leu Ser Leu Phe Met Leu Ser Ala
1               5                   10                  15

Phe Ser Ala

<210> SEQ ID NO 6
<211> LENGTH: 25
<212> TYPE: PRT
<213> ORGANISM: Escherichia coli

<400> SEQUENCE: 6

Met Met Lys His Met Arg Ile Trp Ala Val Leu Ala Ser Phe Leu Val
1               5                   10                  15

Phe Phe Tyr Ile Pro Gln Ser Tyr Ala
            20                  25

<210> SEQ ID NO 7
<211> LENGTH: 18
<212> TYPE: PRT
<213> ORGANISM: Escherichia coli

<400> SEQUENCE: 7

Met Arg Phe Leu Leu Gly Val Leu Met Leu Met Ile Ser Gly Ser Ala
1               5                   10                  15

Leu Ala

<210> SEQ ID NO 8
<211> LENGTH: 23
<212> TYPE: PRT
<213> ORGANISM: Escherichia coli

<400> SEQUENCE: 8

Met Ser Lys Arg Thr Phe Ala Val Ile Leu Thr Leu Leu Cys Ser Phe
1               5                   10                  15

Cys Ile Gly Gln Ala Leu Ala
            20

<210> SEQ ID NO 9
<211> LENGTH: 21
<212> TYPE: PRT
<213> ORGANISM: Escherichia coli

<400> SEQUENCE: 9

Met Ser Asp Thr Glu Pro Cys Phe Met Thr Lys Arg Ser Gly Ser Asn
1               5                   10                  15

Thr Arg Arg Arg Ala
            20

<210> SEQ ID NO 10

```
<211> LENGTH: 19
<212> TYPE: PRT
<213> ORGANISM: Escherichia coli

<400> SEQUENCE: 10

Val Ile Lys Phe Leu Ser Ala Leu Ile Leu Leu Val Thr Thr Ala
1               5                   10                  15

Val Gln Ala

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Tyr Lys Asp Asp Asp Asp
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Lys Asp Asp Asp Asp Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Tyr Lys Asp Asp Asp Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Tyr Pro Tyr Asp Val Pro Asp Tyr Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Ala Tyr Asp Val Pro Asp Tyr Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Asp Val Pro Asp Tyr Ala Ser Leu
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Gln Lys Leu Ile Ser Glu Glu Asp Leu
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Glu Thr Ala Ala Ala Lys Phe Glu Arg Gln His Met Asp Ser
1               5                   10                  15

<210> SEQ ID NO 21
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Gly Lys Pro Ile Pro Asn Pro Leu Leu Gly Leu Asp Ser Thr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ser Gly Arg Gly Gly
1               5

<210> SEQ ID NO 23
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
                20                  25                  30

Leu Ala Leu Ala Ala Asp Met Thr Ile Val Ala Gly Ser Asp Asn Leu
            35                  40                  45

Pro Glu Leu Thr Gly Leu Ala Ile Gly Ala Leu Ile Gly Arg Ser Ala
        50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Ser Val Ile Ala Glu Asp Arg Cys Ala Glu Val Glu Ser
            180                 185                 190

Lys Leu Gly Leu His Tyr Pro Ala Ser Phe Ile Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240
```

```
Ile Asp Leu Ser Phe Ala Ile Leu Arg Ser Val Ser Pro Asn His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Glu Leu Val Ala
    290                 295                 300

Gln Val Leu Ala Trp Gln Ile Gly Val Met Glu Glu
305                 310                 315

<210> SEQ ID NO 24
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atggctgaag gaagcgtcgc acggcagccg gatttactga cgtgtgacga cgaacccata      60 cacataccctg gtgctataca gccacacggt ttacttctgg ctttagctgc ggatatgacc    120
atagtcgctg gtagtgataa cctgcccgaa ttgacgggct tggcgatagg agcccttatt    180
ggccggagtg cagcggacgt gtttgattct gaaacacaca accgtttaac gattgcgctt    240
gcagaaccag gagccgccgt tggtgcccca atcaccgtcg gcttcaccat gagaaaggac    300
gctggcttca tcggttcatg gcacagacat gaccagttga tattttaga attggagccg    360 ccacagagag acgtagcaga gcctcaggct tttttcggc ggacgaactc agctatcaga    420
cgcttacagg cagctgaaac cttggaaagc gcatgtgctg ccgccgctca ggaggtccgt    480
aagataacag ggttcgacag agtgatgatt tatcgttttg cttcggattt ctccgggtcg    540
gtaatagcag aagaccgttg tgcagaagtt gaaagtaaac tgggtcttca ttacccggca    600
tctttcatac cggcacaagc gcgtcgctta tatactataa accctgttcg cattattcca    660
gacatcaatt acagacctgt acctgtaaca cccgatctta acccagtaac gggtcgtccc    720
atcgatttgt ccttcgcgat cttaagaagc gtttcgccta atcaccttga gttcatgcgg    780
aatatcggca tgcatggtac catgagcatc agcattctgc gcggcgagag actttggggt    840 tgatcgtgt gccatcatcg gaccccgtat tatgtagact tagacggtcg gcaagcctgc    900
gagttagtgg cccaagtatt ggcatggcaa ataggtgtaa tggaggaata a            951

<210> SEQ ID NO 25
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Arg Lys Val Asp Leu Thr Ser Cys Asp Arg Glu Pro Ile His
1               5                   10                  15

Ile Pro Gly Ser Ile Gln Pro Cys Gly Cys Leu Leu Ala Cys Asp Ala
            20                  25                  30

Gln Ala Val Arg Ile Thr Arg Ile Thr Glu Asn Ala Gly Ala Phe Phe
        35                  40                  45
```

```
Gly Arg Glu Thr Pro Arg Val Gly Glu Leu Leu Ala Asp Tyr Phe Gly
 50                  55                  60

Glu Thr Glu Ala His Ala Leu Arg Asn Ala Leu Ala Gln Ser Ser Asp
 65                  70                  75                  80

Pro Lys Arg Pro Ala Leu Ile Phe Gly Trp Arg Asp Gly Leu Thr Gly
                 85                  90                  95

Arg Thr Phe Asp Ile Ser Leu His Arg His Asp Gly Thr Ser Ile Ile
                100                 105                 110

Glu Phe Glu Pro Ala Ala Ala Glu Gln Ala Asp Asn Pro Leu Arg Leu
                115                 120                 125

Thr Arg Gln Ile Ile Ala Arg Thr Lys Glu Leu Lys Ser Leu Glu Glu
130                 135                 140

Met Ala Ala Arg Val Pro Arg Tyr Leu Gln Ala Met Leu Gly Tyr His
145                 150                 155                 160

Arg Val Met Leu Tyr Arg Phe Ala Asp Asp Gly Ser Gly Lys Val Ile
                165                 170                 175

Gly Glu Ala Lys Arg Ser Asp Leu Glu Ser Phe Leu Gly Gln His Phe
                180                 185                 190

Pro Ala Ser Leu Val Pro Gln Gln Ala Arg Leu Leu Tyr Leu Lys Asn
                195                 200                 205

Ala Ile Arg Val Val Ser Asp Ser Arg Gly Ile Ser Ser Arg Ile Val
210                 215                 220

Pro Glu His Asp Ala Ser Gly Ala Ala Leu Asp Leu Ser Phe Ala His
225                 230                 235                 240

Leu Arg Ser Ile Ser Pro Ile His Leu Glu Phe Leu Arg Asn Met Gly
                245                 250                 255

Val Ser Ala Ser Met Ser Leu Ser Ile Ile Ile Asp Gly Thr Leu Trp
                260                 265                 270

Gly Leu Ile Ile Cys His His Tyr Glu Pro Arg Ala Val Pro Met Ala
                275                 280                 285

Gln Arg Val Ala Ala Glu Met Phe Ala Asp Phe Leu Ser Leu His Phe
290                 295                 300

Thr Ala Ala His His Gln Arg
305                 310

<210> SEQ ID NO 26
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggctcgga aagtagacct gacatcttgt gaccgtgagc aatacacat cccagggtcg      60 atacaaccct gtgggtgcct tcttgcatgt gacgcacaag ccgtccggat aactcggata    120
acggaaaacg ccggtgcctt ttttggaaga gagacccctc gcgttggtga acttctggca    180
gattactttg gagagacgga agcccatgca ttgagaaatg cactggccca gtcatccgac    240
cccaaaagac ctgcgcttat atttggctgg cgggatggcc ttacaggccg tacgttcgat    300
atatccctgc atagacatga tggtacaagt ataatcgagt tcgaaccggc ggcggcagaa    360
caggcagaca atccattacg ccttactcgg cagattatag cccggacgaa agagttaaaa    420
agtcttgagg atggcagc gagagtgccg agatatttgc aagcaatgtt gggataccac      480
cgggtgatgc tttatagatt cgccgacgat gggtcgggta agtgatcgg tgaagctaaa     540
```

```
agaagtgatt tagagtcctt tctgggccag cattttccag cttccctggt tcctcagcaa      600
gcccgcttgc tgtatttgaa aaatgcaatc cgcgtagtat cagacagccg tggtatatcc      660
tcacggatag taccggagca tgatgcttct ggagctgctc tggatttatc ctttgcacat      720
cttcgcagca taagtcctat ccatttagag ttttttgagaa acatgggggt gtcggcatcc      780
atgtcgttat ccataataat tgacggcaca ctgtgggggc ttattatttg tcatcattac      840
gagccgagag cagttccaat ggcacaacgc gtagctgcag aaatgttcgc tgatttcttg      900
tctctgcact tcactgcagc acatcaccag cgctaa                                936
```

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ggctacatca ttcactttt cttcacaacc ggtccctatc agtgatagag attgacatcc       60
ctatcagtga tagagatact gagcactcta gagtcacaca ggaaagtact ag             112
```

<210> SEQ ID NO 31
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ggctacatca ttcactttt cttcacaacc ggtccctatc agtgatagag attgacatcc       60
ctatcagtga tagagatact gagcactcta gagattaaag aggagaaata ctag           114
```

<210> SEQ ID NO 32
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 32
ggctacatca ttcactttt cttcacaacc ggtttacggc tagctcagtc ctaggtacaa      60
tgctagctct agagtcacac aggaaagtac tag                                  93

<210> SEQ ID NO 33
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggctacatca ttcactttt cttcacaacc ggtttacggc tagctcagtc ctaggtacaa      60
tgctagctct agagattaaa gaggagaaat actag                                95
```

ENGINEERED BACTERIA SECRETING THERAPEUTIC PROTEINS AND METHODS OF USE THEREOF

RELATED APPLICATIONS

This application is a 35 U.S.C. § 371 national stage filing of International Application No. PCT/US2017/049639, filed on Aug. 31, 2017, which in turn claims priority to U.S. Provisional Patent Application No. 62/381,961, filed on Aug. 31, 2016. The entire contents of each of the aforementioned applications are expressly incorporated herein by reference.

SEQUENCE LISTING

The instant application contains a Sequence Listing which has been submitted electronically in ASCII format and is hereby incorporated by reference in its entirety. Said ASCII copy, created on Sep. 25, 2017, is named 117823-14120_SL.TXT and is 15,504 bytes in size.

FIELD

The technology described herein relates to engineered bacteria that secrete therapeutic polypeptides, pharmaceutical compositions comprising the engineered bacteria, methods for producing recombinant polypeptides, and methods for using the engineered bacteria for diagnostic and therapeutic purposes.

BACKGROUND

Recombinant polypeptide production using engineered bacteria has led to significant advances in the medical sciences by allowing for the generation of medically important polypeptides that would otherwise be difficult to obtain from natural sources. Such polypeptides are overexpressed in the engineered bacteria in vitro, isolated and purified for therapeutic use. Additionally, engineered bacteria that express recombinant polypeptides can be used to deliver recombinant polypeptides to subjects in vivo for the diagnosis and treatment of diseases and/or disorders.

However, the expression of some recombinant polypeptides in engineered bacteria, particularly polypeptides containing disulfide bonds, can often be challenging and result in low production yields, or misfolded proteins. Disulfide bond formation is a process mainly restricted to proteins that are generally located outside of the cytoplasm, such as eukaryotic proteins secreted into the lumen of the endoplasmic reticulum (ER), or prokaryotic proteins present in the periplasm of Gram-negative bacteria. Proper protein folding often depends on the formation of disulfide bonds, and improperly folded proteins may not be functionally active. Moreover, engineered bacteria capable of secreting a therapeutic or diagnostic polypeptide that is properly folded must also express sufficient quantities to be clinically effective for in vivo diagnostic and treatment methods.

Accordingly, there is a need in the art for methods of producing recombinant polypeptides at high yields that are properly folded. Moreover, there is also a need in the art for methods of producing engineered bacteria that can be safely administered to a subject, and produce and secrete a therapeutic polypeptide for a variety of medical uses (e.g., diagnostics and therapeutics).

SUMMARY

Further features and advantages of certain embodiments of the present invention will become more fully apparent in the following description of embodiments and drawings thereof, and from the claims.

In one aspect, the provided herein is an engineered bacterium comprising a heterologous nucleic acid, wherein the heterologous nucleic acid comprises a nucleic acid sequence encoding a signal recognition particle (SRP) pathway signal sequence, a nucleic acid sequence encoding a CsgGE export signal sequence, and a nucleic acid sequence encoding a therapeutic polypeptide.

In some embodiments, the CsgGE export signal sequence is an *E. coli* CsgGE export signal sequence. In some embodiments, the CsgGE export signal sequence comprises the amino acid sequence of SEQ ID NO: 1.

In some embodiments, the SRP pathway signal sequence comprises a signal sequence selected from the group consisting of a CcmH signal sequence, a DsbA signal sequence, a FlgI signal sequence, a SfmC signal sequence, a FocC signal sequence, a NikA signal sequence, a TolB signal sequence, a TorT signal sequence, and a YraI signal sequence. In some embodiments, the SRP pathway signal sequence comprises a FlgI signal sequence. In some embodiments, the SRP pathway signal sequence comprises a SfmC signal sequence. In one embodiment, the SRP pathway signal sequence comprises a YraI signal sequence.

In some embodiments, the CsgGE export signal sequence comprises the amino acid sequence of SEQ ID NO:1 and the SRP pathway signal sequence comprises the CcmH signal sequence (SEQ ID NO: 7). In some embodiments, the CsgGE export signal sequence comprises the amino acid sequence of SEQ ID NO:1 and the SRP pathway signal sequence comprises the DsbA signal sequence (SEQ ID NO: 2). In some embodiments, the CsgGE export signal sequence comprises the amino acid sequence of SEQ ID NO:1 and the SRP pathway signal sequence comprises the FlgI signal sequence (SEQ ID NO: 10). In some embodiments, the CsgGE export signal sequence comprises the amino acid sequence of SEQ ID NO:1 and the SRP pathway signal sequence comprises the SfmC signal sequence (SEQ ID NO: 3). In some embodiments, the CsgGE export signal sequence comprises the amino acid sequence of SEQ ID NO:1 and the SRP pathway signal sequence comprises the FocC signal sequence (SEQ ID NO: 6). In some embodiments, the CsgGE export signal sequence comprises the amino acid sequence of SEQ ID NO:1 and the SRP pathway signal sequence comprises the NikA signal sequence (SEQ ID NO: 9). In some embodiments, the CsgGE export signal sequence comprises the amino acid sequence of SEQ ID NO:1 and the SRP pathway signal sequence comprises the TolB signal sequence (SEQ ID NO: 4). In some embodiments, the CsgGE export signal sequence comprises the amino acid sequence of SEQ ID NO:1 and the SRP pathway signal sequence comprises the TorT signal sequence (SEQ ID NO: 5). In some embodiments, the CsgGE export signal sequence comprises the amino acid sequence of SEQ ID NO:1 and the SRP pathway signal sequence comprises the YraI signal sequence (SEQ ID NO: 8).

In one aspect, the provided herein is an engineered bacterium comprising a heterologous nucleic acid, wherein the heterologous nucleic acid comprises a nucleic acid sequence encoding a SecA-dependent secretion signal, a nucleic acid sequence encoding a CsgGE export signal sequence, and a nucleic acid sequence encoding a therapeutic polypeptide.

In some embodiments, the therapeutic polypeptide is selected from the group consisting of an antibody, an antibody fragment, an enzyme, a fusion protein, a hormone, an antigen, a thrombolytic agent, a cytokine, an immunotoxin, and a growth factor. In some embodiments, the antibody fragment is a single domain antibody. In some embodiments, the single domain antibody is derived from an animal selected from the group consisting of a llama, an alpaca, a camel and a shark. In some embodiments, the single domain antibody is specific for an antigen selected from the group consisting of: carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, and *Plasmodium* membrane protein. In some embodiments, the cytokine is selected from the group consisting of IL-1, IL-2, IL-4, IL-5, IL-6, IL-12, IFN-γ, TNF-α, IL-10, TFF2, interferon alpha 2B, and glucagon-like peptide-1 (GLP-1).

In some embodiments, the therapeutic polypeptide is a non-amyloid polypeptide.

In some embodiments, the nucleic acid sequence encoding the SRP pathway signal sequence and the nucleic acid sequence encoding the CsgGE export signal sequence are located N-terminal to the nucleic acid sequence encoding the therapeutic polypeptide.

In some embodiments, the heterologous nucleic acid further comprises a nucleic acid sequence encoding a polypeptide tag. In some embodiments, the polypeptide tag is selected from the group consisting of a poly-histidine tag, a myc tag a FLAG tag, a hemagglutinin (HA) tag, and a V5 tag.

In some embodiments, the engineered bacterium is a non-pathogenic bacterium.

In some embodiments, the engineered bacterium is a bacterium of the genus *Bacteroides* or *Escherichia*. In some embodiments, the engineered bacterium is a probiotic bacterium. In some embodiments, the engineered bacterium is of the species *Escherichia coli*. In some embodiments, the engineered bacterium is of the species *Escherichia coli* strain Nissle 1917. In some embodiments, the engineered bacterium is of the species *Escherichia coli* strain K-12. In some embodiments, the engineered bacterium is of the species *Escherichia coli* strain K12 W3110.

In some embodiments, the engineered bacterium further comprises a heterologous csgE gene. In some embodiments, the engineered bacterium further comprises a heterologous csgG gene. In some embodiments, the engineered bacterium further comprises a heterologous ffh gene. In some embodiments, the engineered bacterium further comprises a heterologous ftsY gene. In some embodiments, the engineered bacterium further comprises a heterologous ffs gene.

In some embodiments, the engineered bacterium comprises a native csgE gene. In some embodiments, the engineered bacterium comprises a native csgG gene. In some embodiments, the engineered bacterium comprises a native ffh gene. In some embodiments, the engineered bacterium comprises a native ftsY gene. In some embodiments, the engineered bacterium comprises a native ffs gene.

In some embodiments, the engineered bacterium comprises a genetic modification in a csgA gene. In some embodiments, the genetic modification is selected from the group consisting of a point mutation, a partial deletion, and a knockout.

In some embodiments, the heterologous nucleic acid is operably linked to a constitutive promoter. In some embodiments, the heterologous nucleic acid is operably linked to an inducible promoter. In some embodiments, the inducible promoter is responsive to an inducer selected from the group consisting of IPTG, arabinose, and tetracycline.

In some embodiments, the heterologous nucleic acid is located in the bacterial chromosome. In some embodiments, the heterologous nucleic acid is located in a plasmid. In some embodiments, the plasmid comprises a selectable marker gene. In some embodiments, the selectable marker gene expresses a protein that confers the engineered bacterium resistance to an antibiotic. In some embodiments, the plasmid lacks a selectable marker gene. In some embodiments, the plasmid is pMUT1 or pMUT2. In some embodiments, the plasmid further comprising a nucleic acid encoding a detectable protein. In some embodiments, the detectable protein is a fluorescent protein. In some embodiments, the detectable protein is a near infrared fluorescent protein.

In another aspect, provided herein is a pharmaceutical composition comprising the engineered bacterium described herein, and a pharmaceutically acceptable excipient.

In some embodiments, the pharmaceutical composition is formulated for oral administration to a subject. In some embodiments, the pharmaceutical composition is formulated for rectal administration to a subject. In some embodiments, the pharmaceutical composition is formulated as a pill, a capsule, a lozenge or a suppository.

In yet another aspect, provided herein are methods of producing a recombinant polypeptide, comprising culturing the engineered bacterium described herein under conditions suitable for expression and export of the recombinant polypeptide from the engineered bacterium, wherein the recombinant polypeptide comprises the CsgGE export signal sequence and the therapeutic polypeptide.

In some embodiments, the recombinant polypeptide is not toxic to the engineered bacterium.

In some embodiments, inclusion bodies comprising the recombinant polypeptide are not formed during expression and export of the recombinant polypeptide in the engineered bacterium.

In some embodiments, protein aggregates comprising the recombinant polypeptide are not formed during or after expression and export of the recombinant polypeptide from the engineered bacterium.

In some embodiments, the level of expression and export of the recombinant polypeptide is increased by at least 2-fold, as compared to the level of expression and export of the recombinant polypeptide expressed from a heterologous nucleic acid sequence lacking the nucleic acid sequence encoding the SRP pathway signal sequence and/or lacking the nucleic acid sequence encoding the CsgGE export signal sequence, from an engineered bacterium under the same conditions. In some embodiments, the level of expression and export of the recombinant polypeptide is increased by at least 3-fold, 4-fold, or 5-fold.

In some embodiments, the methods further comprise collecting the recombinant polypeptide from cell culture medium comprising the engineered bacterium.

In some embodiments, the engineered bacterium is not exposed to a lysing agent prior to collecting the recombinant protein from the cell culture medium.

In some embodiments, the recombinant polypeptide is collected from a supernatant of the cell culture medium.

In some embodiments, the methods further comprise purifying the recombinant polypeptide.

In another aspect, provided herein is a recombinant polypeptide produced using the methods described herein.

In yet another aspect, provided herein are methods for treating a disease or disorder in a subject, the method comprising administering an engineered bacterium or a pharmaceutical composition described herein to the subject, wherein the engineered bacterium expresses and exports a recombinant polypeptide comprising the CsgGE export signal sequence and the therapeutic polypeptide, thereby treating the disease or disorder in the subject.

In some embodiments, the engineered bacterium is administered orally. In some embodiments, the engineered bacterium is administered rectally.

In some embodiments, the subject is mammalian subject. In some embodiments, the mammalian subject is a human subject.

In some embodiments, the disease or disorder is a gastrointestinal disease or disorder. In some embodiments, the gastrointestinal disease or disorder is selected from the group consisting of inflammatory bowel disease, Crohn's disease, ulcerative colitis, colorectal cancer, ulcer, malabsorption, short-gut syndrome, cul-de-sac syndrome, celiac sprue, tropical sprue, hypogammaglobulinemic sprue, enteritis, short bowel syndrome, and gastrointestinal cancer.

In some embodiments, the disease or disorder is a systemic disease or disorder. In some embodiments, the disease or disorder is selected from the group consisting of an allergy, an autoimmune disease, asthma, rheumatoid arthritis, diabetes, lupus, a viral infection, a bacterial infection, a protozoal infection, a fungal infection, cancer, multiple sclerosis, a congenital genetic disorder, a tissue or organ trauma, toxin ingestion, heavy metal poisoning, aging, and a metabolic disorder.

In another aspect, provided herein is a vector comprising a heterologous nucleic acid, wherein the heterologous nucleic acid comprises a nucleic acid sequence encoding a signal recognition particle (SRP) pathway signal sequence, a nucleic acid sequence encoding a CsgGE export signal sequence, and a nucleic acid sequence encoding a therapeutic polypeptide.

In some embodiments, the CsgGE export signal sequence is an *E. coli* CsgGE export signal sequence. In some embodiments, the CsgGE export signal sequence comprises the amino acid sequence of SEQ ID NO: 1.

In some embodiments, the SRP pathway signal sequence comprises a signal sequence selected from the group consisting of a CcmH signal sequence, a DsbA signal sequence, a FlgI signal sequence, a FocC signal sequence, a NikA signal sequence, a TolB signal sequence, a TorT signal sequence, a SfmC signal sequence, and a YraI signal sequence.

In some embodiments, the SRP pathway signal sequence comprises a FlgI signal sequence. In some embodiments, the SRP pathway signal sequence comprises a SfmC signal sequence. In some embodiments, the SRP pathway signal sequence comprises a YraI signal sequence.

In some embodiments, the therapeutic polypeptide is selected from the group consisting of an antibody, an antibody fragment, an enzyme, a fusion protein, a hormone, an antigen, a thrombolytic agent, a cytokine, an immunotoxin, and a growth factor. In some embodiments, the antibody fragment is a single domain antibody. In some embodiments, the single domain antibody is derived from an animal selected from the group consisting of a llama, an alpaca, a camel and a shark.

In some embodiments, the single domain antibody is specific for an antigen selected from the group consisting of: carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, and *Plasmodium* membrane protein.

In some embodiments, the therapeutic polypeptide is a non-amyloid polypeptide.

In some embodiments, the nucleic acid sequence encoding the SRP pathway signal sequence and the nucleic acid sequence encoding the CsgGE export signal sequence are located N-terminally to the nucleic acid sequence encoding the therapeutic polypeptide.

In some embodiments, the heterologous nucleic acid further comprises a nucleic acid sequence encoding a polypeptide tag.

In some embodiments, the polypeptide tag is selected from the group consisting of a poly-histidine tag, a myc tag a FLAG tag, a hemagglutinin (HA) tag, and a V5 tag.

In some embodiments, the heterologous nucleic acid is operably linked to a constitutive promoter. In some embodiments, the heterologous nucleic acid is operably linked to an inducible promoter. In some embodiments, the inducible promoter is responsive to an inducer selected from the group consisting of IPTG, arabinose, and tetracycline. In some embodiments, the vector backbone is pMUT1 or pMUT2.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DETAILED DESCRIPTION

Figure 1:
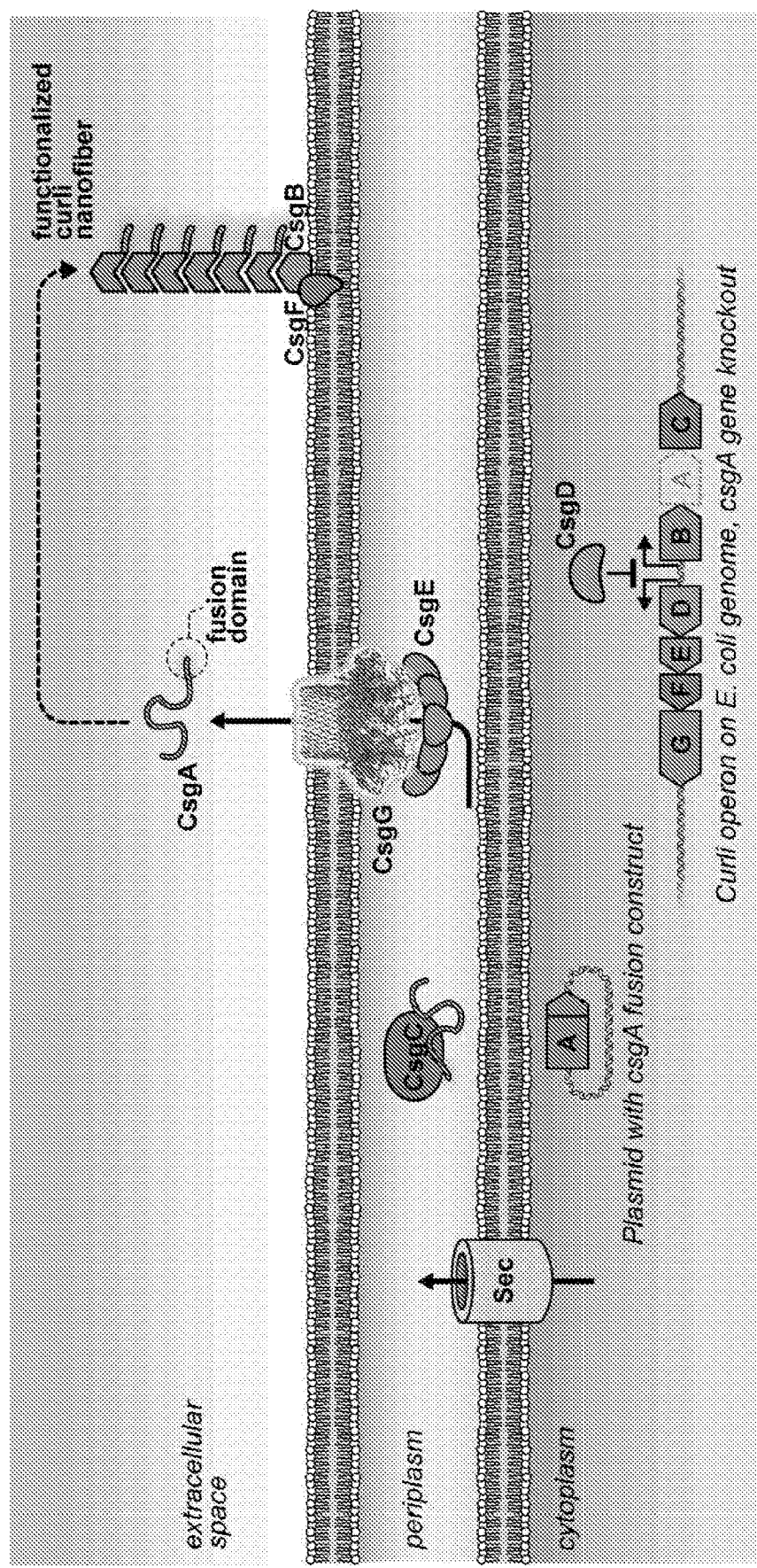
FIG. 1 is a diagram depicting the native curli system in which CsgA gene has been placed under episomal control. Protein secretion occurs via the SEC translocon, which mediates protein transport to the bacterial periplasm, and the type-8 bacterial secretion system (T8SS), which includes the proteins CsgG and CsgE that mediate export of proteins from the periplasm into the extracellular milieu.
Figure 2:
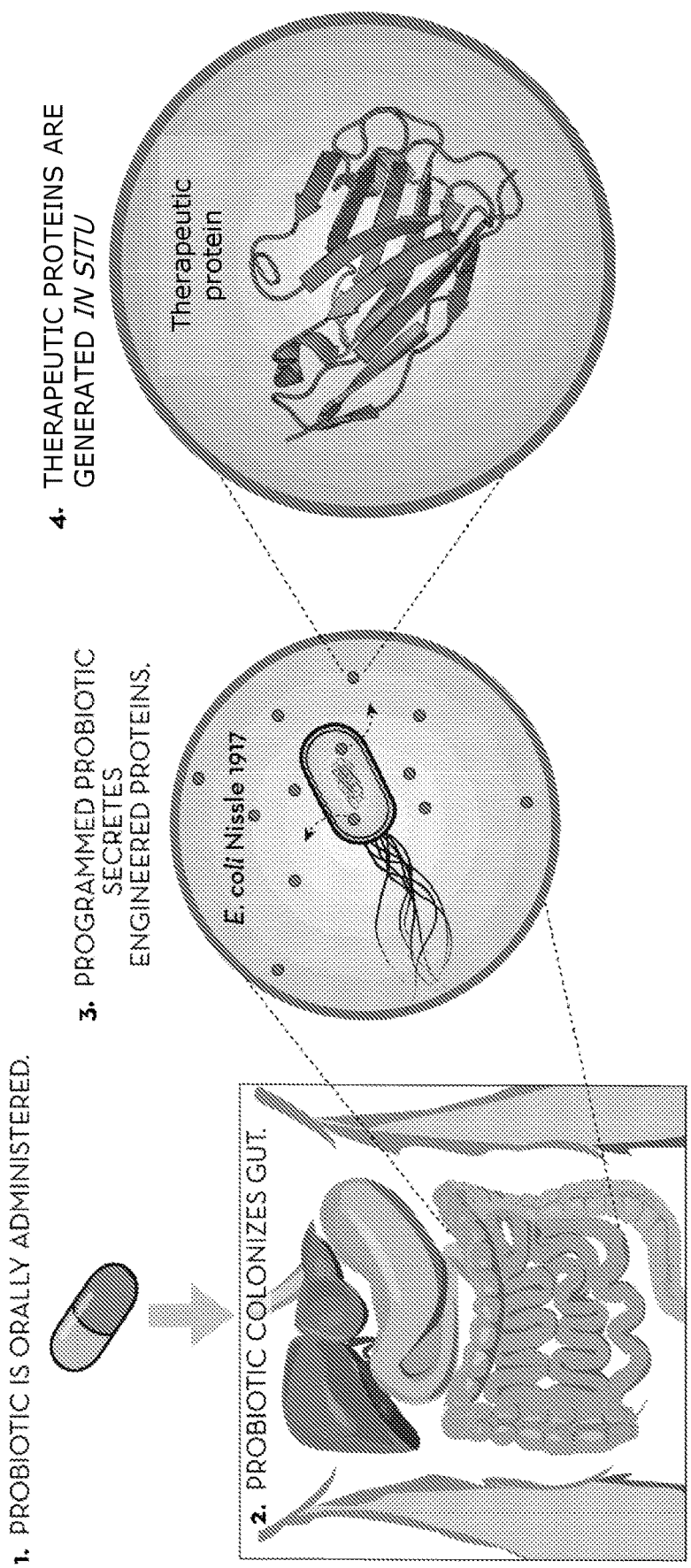
FIG. 2 depicts a pharmaceutical composition comprising engineered bacteria described herein, which express an exemplary therapeutic polypeptide, a single-domain antibody.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Definitions

As used herein, the term "engineered bacterium" or "engineered bacterial cell" refers to a bacterial cell that has been genetically modified from its native state. For instance, an engineered bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Engineered bacterial cells of the disclosure may comprise exogenous nucleotide sequences on plasmids. Alternatively, recombinant bacterial cells may comprise exogenous nucleotide sequences stably incorporated into their chromosome. In some embodiments, the engineered bacterium is non-pathogenic. In some embodiments, the engineered bacterium is pathogenic.

"Probiotic", as used herein, refers to a live, non-pathogenic microorganism, e.g., a bacterium, which can confer health benefits to a host organism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, *Bacteroides* (e.g., *Bacteroides fragilis, Bacteroides subtilis*, and *Bacteroides thetaiotaomicron*) and *Escherichia coli*. In some embodiments, the probiotic is Gram-negative bacterium. The probiotic may be a variant or a mutant strain of bacterium. Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

The term "antibody", as used herein, refers to any immunoglobulin (Ig) molecule comprised of four polypeptide chains, two heavy (H) chains and two light (L) chains, or any functional fragment, mutant, variant, or derivation thereof. Such mutant, variant, or derivative antibody formats are known in the art. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody is a full-length antibody. In some embodiments, the antibody is a murine antibody. In some embodiments, the antibody is a human antibody. In some embodiments, the antibody is a humanized antibody. In other embodiments, the antibody is a chimeric antibody. Chimeric and humanized antibodies may be prepared by methods well known to those of skill in the art including CDR grafting approaches (see, e.g., U.S. Pat. Nos. 5,843,708; 6,180,370; 5,693,762; 5,585,089; and 5,530,101), chain shuffling strategies (see, e.g., U.S. Pat. No. 5,565,332; Rader et al. (1998) PROC. NAT'L. ACAD. SCI. USA 95: 8910-8915), molecular modeling strategies (U.S. Pat. No. 5,639,641), and the like.

In some embodiments, the antibody is a donkey antibody. In some embodiments, the antibody is a rat antibody. In some embodiments, the antibody is a horse antibody. In some embodiments, the antibody is a camel antibody. In some embodiments, the antibody is a shark antibody.

The term "antigen-binding portion" of an antibody (or simply "antibody fragment"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Examples of antibody fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341: 544-546; and PCT Publication No. WO 90/05144 A1, the contents of which are herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Nat'l. Acad. Sci. USA 85:5879-5883). Such single chain antibodies are also intended to be encompassed within the term "antigen-binding portion" of an antibody. Other forms of single chain antibodies, such as diabodies are also encompassed. Antibody fragments also include single domain antibodies, maxibodies, minibodies, nanobodies, intrabodies, diabodies, triabodies, tetrabodies, v-NAR and bis-scFv (see, e.g., Hollinger and Hudson (2005) Nature Biotechnology 23:1126-1136).

A "single domain antibody", as used herein, refers to the heavy chain variable domain ("VH") of an antibody, i.e., a heavy chain variable domain without a light chain variable domain. Single domain antibodies are described, for example, in Hamers-Casterman et al. (1993) Nature 363: 446-48, and Dumoulin et al. (2002) Protein Science 11:500-15. Single domain antibodies can be derived from a multiple animals, including, for example, llama, alpaca, camel (i.e., camelid single domain antibodies), and shark.

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence.

As used herein, a "heterologous" gene, "heterologous sequence", or "heterologous nucleic acid" refers to a nucleic acid sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. A heterologous gene may include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature.

As used herein, the term "endogenous gene" refers to a native gene in its natural location in the genome of an organism.

As used herein, the term "transgene" refers to a gene that has been introduced into the host organism, e.g., host bacterial cell's genome.

As used herein, a "SecA-dependent secretion signal", refers to a polypeptide sequence which, when present on a polypeptide, e.g., at the N-terminus of a polypeptide, can cause the polypeptide to be exported from the cytoplasm of a bacterium across the inner membrane as mediated by a bacterial SEC system. In some embodiments, the SecA-dependent secretion signal is the polypeptide having the sequence of the E. coli CsgA SecA-dependent secretion signal and homologs and/or variants, including conservative substitution variants, thereof.

As used herein, a "signal recognition particle (SRP) pathway signal sequence" refers to a polypeptide sequence which, when present on a polypeptide (e.g., the N-terminus of a polypeptide), can cause the polypeptide to be exported from the cytoplasm of a bacterial cell across the inner membrane as mediated by the single recognition particle (SRP) pathway proteins. In some embodiments, the polypeptide is translated and transported across the inner membrane concurrently, thus guiding the nascent polypeptide into the periplasm. In some embodiments, the SRP pathway signal sequence is the SRP signal sequence from CcmH, DsbA, FocC, NikA, SfmC, TolB, TorT, YraI, or homologs and/or variants, including conservative substitution variants, thereof.

As used herein, a "CsgE export signal sequence" refers to a polypeptide sequence which, when present at the N-terminus of a polypeptide can cause the polypeptide to be targeted by CsgE and exported across the outer membrane of the cell via the CsgG oligomeric transport complex of a curli export system, or by an orthologous export system. In some embodiments, the CsgG targeting sequence is the last 22 amino acids of the bipartite curli signal sequence of an endogenous polypeptide exported by the curli export system. In some embodiments, the CsgG targeting sequence can be a polypeptide having the sequence of an E. coli CsgA CsgGE export signal sequence (e.g., SEQ ID NO: 1) and homologs and/or variants, including conservative substitution variants, thereof.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell-specific or tissue-specific manner, in response to different environmental or physiological conditions, or in response to specific compounds. Prokaryotic promoters are typically classified into two classes: inducible and constitutive.

"Constitutive promoter" refers to a promoter that is capable of facilitating continuous transcription of a coding sequence or gene under its control and/or to which it is operably linked. Constitutive promoters and variants are well known in the art and include, but are not limited to, a constitutive Escherichia coli $\sigma^S$ promoter, a constitutive Escherichia coli $\sigma^{32}$ promoter, a constitutive Escherichia coli $\sigma^{70}$ promoter, a constitutive Bacillus subtilis $\sigma^A$ promoter, a constitutive Bacillus subtilis $\sigma^B$ promoter, and a bacteriophage T7 promoter.

An "inducible promoter" refers to a promoter that initiates increased levels of transcription of the coding sequence or gene under its control in response to a stimulus or an exogenous environmental condition. A "directly inducible promoter" refers to a regulatory region, wherein the regulatory region is operably linked to a gene encoding a protein or polypeptide, where, in the presence of an inducer of said regulatory region, the protein or polypeptide is expressed. An "indirectly inducible promoter" refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by "inducible promoter."

As used herein, the term "expression" refers to the transcription and stable accumulation of sense (mRNA) or anti-sense RNA derived from a nucleic acid, and/or to translation of an mRNA into a polypeptide The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising at least one amino acid catabolism enzyme operably linked to a promoter, into a bacterial cell. Genetic modification can also involve a targeted replacement in the chromosome, e.g., to replace a native gene promoter with an inducible promoter, regulated promoter, strong promoter, or constitutive promoter. Genetic modification can also involve gene amplification, e.g., introduction of at least one additional copy of a native gene into the chromosome of the cell. Alternatively, chromosomal genetic modification can involve a genetic mutation.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein, the term "exogenous" refers to a substance (e.g., a nucleic acid or polypeptide) present in a cell other than its native source. The term exogenous can refer to a nucleic acid or a protein that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" refers to a substance that is native to the biological system or cell.

A "non-amyloid polypeptide", as used herein, refers to a polypeptide that does not form amyloid aggregates in a cell (e.g., a bacterial cell). An "amyloidogenic polypeptide" refers to a peptide that either forms or increases the formation of amyloid aggregates in a cell. In some embodiments, the therapeutic polypeptide is a non-amyloid polypeptide. In some embodiments, the polypeptide is a non-amyloidogenic polypeptide. An "amyloid polypeptide" refers to a polypeptide that forms amyloid aggregates in a bacterial cell. A "amyloidogenic polypeptide" refers to a polypeptide that either forms or increases the formation of amyloid aggregates in a cell. In some embodiments, the therapeutic polypeptide is an amyloid polypeptide. In some embodiments, the therapeutic polypeptide is an amyloidogenic polypeptide.

A "pharmaceutical composition," as used herein, refers to a composition comprising an active ingredient (e.g., a bacterial cell, an inducer, a drug, or a detectable compound) with other components such as a physiologically suitable carrier and/or excipient.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by the FDA Office of Biological Standards.

As used herein, the term "pharmaceutically acceptable excipient" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

A "plasmid" or "vector" includes a nucleic acid construct designed for delivery to a host cell or transfer between different host cell. An "expression plasmid" or "expression vector" can be a plasmid that has the ability to incorporate and express heterologous nucleic acid fragments in a cell. An expression plasmid may comprise additional elements, for example, the expression vector may have two replication systems, thus allowing it to be maintained in two organisms. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. The terms "protein" and "polypeptide" as used herein refer to both large polypeptides and small peptides. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "therapeutic polypeptide" refers to any polypeptide that has a therapeutic effect or may be used for diagnostic purposes when introduced into a eukaryotic organism (e.g., a mammalian subject such as human). In some embodiments, the therapeutic polypeptide is an antibody. In some embodiments, the therapeutic polypeptide is a single domain antibody. In some embodiments, the therapeutic polypeptide is a fusion protein, a hormone, an antigen, a thrombolytic agent, a cytokine or a growth factor. In some embodiments the therapeutic polypeptide is an immunotoxin (e.g., an antibody fused to a cellular toxin).

The term "operatively linked" includes having an appropriate transcription start signal (e.g., promoter) in front of the polynucleotide sequence to be expressed, and having an appropriate translation start signal (e.g., a Shine Delgarno sequence and a start codon (ATG)) in front of the polypeptide coding sequence and maintaining the correct reading frame to permit expression of the polynucleotide sequence under the control of the expression control sequence, and, optionally, production of the desired polypeptide encoded by the polynucleotide sequence. In some examples, transcription of a gene encoding a recombinant polypeptide as described herein is under the control of a promoter sequence (or other transcriptional regulatory sequence) which controls the expression of the nucleic acid in a cell-type in which expression is intended. It will also be understood that the gene encoding a recombinant polypeptide as described herein can be under the control of transcriptional regulatory sequences which are the same or which are different from those sequences which control transcription of the naturally-occurring form of a protein.

The terms "overexpression" or "overexpress", as used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. In some embodiments, the terms can represent a 100% decrease, i.e. a non-detectable level as compared to a reference level. In the context of a marker or symptom, a "decrease" is a statistically significant decrease in such level. The decrease can be, for example, at least 10%, at least 20%, at least 30%, at least 40% or more, and is preferably down to a level accepted as within the range of normal for an individual without such disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

The term "non-pathogenic" as used herein to refer to bacteria refers to bacteria that are not capable of causing disease or harmful responses in a host. In some embodiments, non-pathogenic bacteria are commensal bacteria. Examples of non-pathogenic bacteria include, but are not limited to *Bacteroides* and *Escherichia coli*, e.g., *Escherichia coli* Nissle 1917, *Bacteroides fragilis*, *Bacteroides subtilis*, and *Bacteroides* thetaiotaomicron. Naturally pathogenic bacteria may be genetically engineered to provide reduce or eliminate pathogenicity.

As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, polypeptide described herein can be a variant of a sequence described herein, e.g., a conservative substitution variant of a polypeptide comprising the amino acid sequence of SEQ ID NO: 1. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g. ability to target a polypeptide for export via the curli export system. A wide variety of PCR-based site-specific mutagenesis approaches are also known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence, e.g., SEQ ID NO:1. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Engineered Bacteria

In one aspect, provided herein are engineered bacteria that have been genetically modified to comprise a heterologous nucleic acid comprising a nucleic acid sequence encoding a signal recognition particle (SRP) pathway signal sequence, a nucleic acid sequence encoding a CsgGE export signal sequence, and a nucleic acid sequence encoding a therapeutic polypeptide. In another aspect, the engineered bacteria have been genetically modified to comprise a heterologous nucleic acid, wherein the heterologous nucleic acid comprises a nucleic acid sequence encoding a SecA-dependent secretion signal, a nucleic acid sequence encoding a CsgGE export signal sequence, and a nucleic acid sequence encoding a therapeutic polypeptide. The use of the genetically-modified bacteria described herein to express any therapeutic polypeptide of interest beneficially results in the production of therapeutic peptides that are properly folded in the periplasm of the bacteria, and can thus be used in a variety of applications, including therapeutic applications.

In some embodiments, the heterologous nucleic acid comprises a nucleic acid encoding a CsgGE export signal sequence. The CsgGE export signal sequence facilitates the transport of a polypeptide comprising the CsgGE export signal sequence from the bacterial periplasm via a bacterial type-8 secretion system. The Type-8 Secretion System (T8SS) of Gram-negative bacteria, such as *Escherichia coli*, is a dedicated protein export system that has evolved for the secretion of functional amyloids (e.g., an amyloid polypeptide) to the extracellular space. These amyloids then self-assemble to form nanofibers implicated in pathogenesis of epithelial tissue and biofilm persistence (Chapman et al. 2002). The outer membrane porin for the T8SS is composed of nonameric outer membrane protein, CsgG. The fully assembled CsgG complex contains a 2 nm transmembrane channel (Goyal et al. 2014). The structural monomeric unit of the functional amyloid, CsgA, is exported to the extracellular space via CsgG through a specific CsgG-specific N-terminal peptide tag, called N22. This event is preceded by translocation of the cytoplasmically-expressed CsgA protein to the periplasm through the Sec system, the major periplasmic export system in bacteria. An additional periplasmically-localized protein, CsgE, confers N22-containing substrate specificity for CsgG export and forms a multimeric complex with CsgG, encapsulating the protein to be exported and creating an entropic free-energy gradient that is thought to drive the export through the CsgG channel. In the absence of CsgE, the CsgG porin is ungated, allowing for passive diffusion of molecules through the outer membrane (Nenninger et al. 2011).

In some embodiments, the CsgGE export signal sequence is an *E. coli* CsgGE export signal sequence. In some embodiments, the *E. coli* CsgGE export signal sequence comprises the amino acid sequence GVVPQYGGGG-NHGGGGNNSGPN (SEQ ID NO: 1; referred to herein as N22).

Any CsgGE export signal sequence known in the art and homologs and/or variants, including conservative substitution variants, may be used as described herein. For example, an export signal sequence that mediates the export of a polypeptide to the extracellular milieu that is orthologous to a curli export system may be used as described herein. In some embodiments, the nucleic acid sequence encoding the CsgGE export signal sequence is upstream of the nucleic acid encoding the therapeutic polypeptide. In some embodiments, the nucleic acid encoding the CsgGE export signal sequence is upstream of the nucleic acid encoding the SRP pathway signal sequence. In some embodiments, the nucleic acid encoding the CsgGE export signal sequence is downstream of the nucleic acid sequence encoding the SRP pathway signal sequence.

In some embodiments, the heterologous nucleic acid comprises a nucleic acid sequence encoding a SRP pathway signal sequence. The SRP pathway is a polypeptide transport system in bacterial cells which mediates the co-translational translocation of proteins through the inner membrane and into the periplasm. In the SRP system, a specific N-terminal protein sequence is recognized by a complex comprising, Ffh protein and a 4.5S RNA, which guides the nascent polypeptide chain directly into the periplasm. Thus, protein folding occurs in the periplasm, avoiding folding-unfolding obstacles that may arise when a protein is transported across the inner-membrane post-translationally (e.g., using a Sec-mediated transport pathway). In some embodiments, the SRP pathway signal sequence is cleavable (see, e.g., Schierle et al. (2003) *J. Bacteriol.* 185(19): 5706-13). Any known SRP pathway signal sequences can be used as described herein. In some embodiments, the SRP signal sequence comprises a CcmH, DsbA, FlgI, FocC, NikA, SfmC, TolB, TorT, YraI signal sequence, or homologs and/or variants, including conservative substitution variants, thereof. In some embodiments, the SRP signal sequence comprises the amino acid sequence of any one of SEQ ID NOs: 2-10, or homologs and/or variants, including conservative substitution variants, thereof. In some embodiments, the SRP pathway signal sequence comprises a FlgI signal sequence. In some embodiments, the SRP pathway signal sequence comprises a SfmC signal sequence. In some embodiments, the SRP pathway signal sequence comprises a YraI signal sequence.

TABLE 1

Exemplary SRP pathway signal sequences

| SRP pathway signal sequence name | Amino Acid Sequence |
|---|---|
| DsbA (Nissle) | MKKIWLALAGLVLAFSASA (SEQ ID NO: 2) |
| SfmC (W3110) | MMTKIKLLMLIIFYLIISASAHA (SEQ ID NO: 3) |
| TolB (Nissle) | MKQALRVAFGFLILWASVLHA (SEQ ID NO: 4) |
| TorT (Nissle) | MRVLLFLLLSLFMLSAFSA (SEQ ID NO: 5) |
| FocC (Nissle) | MMKHMRIWAVLASFLVFFYIPQSYA (SEQ ID NO: 6) |

TABLE 1-continued

Exemplary SRP pathway signal sequences

| SRP pathway signal sequence name | Amino Acid Sequence |
|---|---|
| CcmH (Nissle) | MRFLLGVLMLMISGSALA (SEQ ID NO: 7) |
| YraI (W3110) | MSKRTFAVILTLLCSFCIGQALA (SEQ ID NO: 8) |
| NikA (Nissle) | MSDTEPCFMTKRSGSNTRRRA (SEQ ID NO: 9) |
| FlgI (Nissle) | VIKFLSALILLLVTTAVQA (SEQ ID NO: 10) |

The heterologous nucleic acids described herein may comprise a nucleic acid sequence encoding any combination of a SRP pathway signal sequence, a CsgGE export signal sequence and a therapeutic polypeptide. In some embodiments, the heterologous nucleic acid comprises multiple nucleic acid sequences encoding a SRP pathway signal sequence (e.g., one, two, three, four, five, or six nucleic acid sequences encoding a SRP pathway signal sequence). In some embodiments, the heterologous nucleic acid comprises multiple nucleic acid sequences encoding a CsgGE export signal sequence (e.g., one, two, three, four, five, or six nucleic acid sequences encoding a CsgGE export signal sequence).

In some embodiments, the heterologous nucleic acid comprises a nucleic acid sequence encoding a SecA-dependent secretion signal sequence.

In some embodiments, the heterologous nucleic acid comprises a nucleic acid sequence encoding a therapeutic polypeptide. Any therapeutic polypeptide may be expressed using the genetically-engineered bacteria described herein. In some embodiments, the therapeutic polypeptide is an antibody, an antibody fragment, an enzyme, a fusion protein, a hormone, an antigen, a thrombolytic agent, a cytokine, or a growth factor. In some embodiments, the therapeutic polypeptide is an antibody. In some embodiments, the antibody fragment is a single domain antibody.

In some embodiments, the heterologous nucleic acid comprises a nucleic acid encoding a polypeptide linker sequence between the nucleic acid encoding a CsgGE export signal sequence and a nucleic acid sequence encoding a SRP pathway signal sequence. In some embodiments, the heterologous nucleic acid comprises a nucleic acid encoding a polypeptide linker sequence between the nucleic acid encoding a CsgGE export signal sequence and a nucleic acid sequence encoding a therapeutic polypeptide. In some embodiments, the polypeptide linker sequence comprises the amino acid sequence ASGRGG (SEQ ID NO: 22). In some embodiments, the polypeptide linker sequence has the amino acid sequence ASGRGG (SEQ ID NO: 22).

The engineered bacterium described herein are particularly suitable for the expression of proteins comprising a stabilizing disulfide bond (e.g., an antibody or an antibody fragment such as a single domain antibody) because SRP-mediated translocation of the nascent protein into the bacterial periplasm as it is being translated allows for proper protein folding to occur under the oxidizing conditions of the bacterial periplasm, approximating the mammalian expression environment and minimizing any off-pathway protein misfolding. In some embodiments, the single domain antibody is derived from a llama, an alpaca, a camel, or a shark. In some embodiments, the single domain antibody is specific for an antigen selected from the group consisting of: carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, and *Plasmodium* membrane protein.

In some embodiments, the therapeutic polypeptide is a non-amyloid polypeptide. In some embodiments, the therapeutic polypeptide is a non-amyloidogenic polypeptide. In some embodiments, the therapeutic polypeptide is a amyloid polypeptide. In some embodiments, the therapeutic polypeptide is a amyloidogenic polypeptide.

In some embodiments, the heterologous nucleic acid comprises a nucleic acid sequence encoding a polypeptide tag. Multiple polypeptide tags are known in the art and can be used as described herein. The polypeptide tag may be used to separate and/or purify the protein encoded by the heterologous nucleic acid. The polypeptide tag may also be used to detect the protein encoded by the heterologous nucleic acid. The nucleic acid sequence encoding the polypeptide tag may be located, in-frame, at any position in the open reading frame of the heterologous nucleic acid. In some embodiments, the nucleic acid sequence encoding the polypeptide tag is upstream from the nucleic acid encoding the therapeutic polypeptide. In some embodiments, the nucleic acid sequence encoding the polypeptide tag is located downstream from the nucleic acid sequence encoding the therapeutic polypeptide. In some embodiments, the polypeptide tag is a poly-histidine tag, a myc tag, a FLAG tag, a hemagglutinin (HA) tag, or a V5 tag. In some embodiments, the heterologous nucleic acid comprises a single nucleic acid sequence encoding a polypeptide tag. In some embodiments, the heterologous nucleic acid comprises more than one nucleic acid sequence encoding a polypeptide tag. In some embodiments, the heterologous nucleic acid comprises a nucleic acid encoding a linker sequence between the nucleic acid sequence encoding the therapeutic polypeptide tag and the nucleic acid sequence encoding the polypeptide tag. Exemplary polypeptide tags for use in the methods described herein include, but are not limited to, the polypeptide tags shown in Table 2.

TABLE 2

Exemplary polypeptide tags

| Tag | Epitope |
|---|---|
| CBP | KRRWKKNFIAVSAANRFKKISSSGAL (SEQ ID NO: 11) |
| FLAG | DYKDDDD (SEQ ID NO: 12) or DYKDDDDK (SEQ ID NO: 13) or DYKDDDK (SEQ ID NO: 14) |
| HA | YPYDVPDYA (SEQ ID NO: 15) or YAYDVPDYA (SEQ ID NO: 16) or YDVPDYASL (SEQ ID NO: 17) |
| Myc | EQKLISEEDL (SEQ ID NO: 18) |
| poly His | HHHHHH (SEQ ID NO: 19) |
| S-tag | KETAAAKFERQHMDS (SEQ ID NO: 20) |
| V5 | GKPIPNPLLGLDST (SEQ ID NO: 21) |

In some embodiments, the heterologous nucleic acid sequence comprises nucleic acid sequence encoding a protease cleavage site amino acid sequence. In some embodiments, the nucleic acid encoding the protease cleavage site amino acid sequence is located between the nucleic acid sequence encoding the CsgGE export signal sequence and the nucleic acid sequence encoding the therapeutic polypeptide. In some embodiments, the nucleic acid encoding the protease cleavage site amino acid sequence is located between the nucleic acid sequence encoding the SRP pathway signal sequence and the nucleic acid sequence encoding the therapeutic polypeptide. In some embodiments, the nucleic acid sequence encoding the protease cleavage site amino acid sequence is located between the nucleic acid sequence encoding the CsgGE export signal sequence and the nucleic acid sequence encoding the SRP pathway signal sequence. In some embodiment, the nucleic acid sequence encoding the protease cleavage site is located between the polypeptide tag and the therapeutic polypeptide.

In some embodiments, the heterologous nucleic acid located in the bacterial chromosome. In some embodiments, the heterologous nucleic acid is located in a plasmid.

In one aspect, provided herein are polypeptides encoded by a heterologous nucleic acid described herein (e.g., a therapeutic polypeptide).

In one aspect, described herein are vectors comprising a heterologous nucleic acid described herein (e.g., a heterologous nucleic acid comprising a nucleic acid sequence encoding a signal recognition particle (SRP) pathway signal sequence, a nucleic acid sequence encoding a CsgGE export signal sequence, and a nucleic acid sequence encoding a therapeutic polypeptide.

In one embodiment, the vector backbone is pMUT1. In one embodiment, the vector backbone is pMUT2. *E. coli* Nissle 1917 contains two high-copy cryptic plasmids, pMUT1 and pMUT2 that are specific for the strain. As discussed below, these plasmids are able to persist in *E. coli* Nissle 1917 without antibiotic selection, suggesting the presence of a genetic mechanism responsible for plasmid retention (see, e.g., Kleta et al. (2014)).

The present inventors have surprisingly discovered that heterologous nucleic acids encoding the protein of interest can be incorporated into pMUT1 or pMUT2, stably transfected into bacterial cells, and retained in the cells for the production of a protein of interest without the need to use a selectable marker (e.g., an antibiotic). The ability to stably transfect bacterial cells, including the probiotic *E. coli* Nissle 1917 without the use of a selectable marker (e.g., an antibiotic) is particularly advantageous for the production of recombinant proteins, as it reduces cross-contamination of recombinant proteins with antibiotics and reduces manufacturing costs. In addition, in the field of probiotic therapeutics, the therapeutic administration of genetically engineered probiotics to a subject without the need to administer a selectable marker (e.g., an antibiotic) allows for the prolonged therapeutic efficacy of an administered genetically engineered probiotic and for a reduction in the potentially deleterious effects of long term administration of the selectable marker which may affect the microbial flora of the subject.

In some embodiments, the pMUT1 plasmid is genetically modified to comprise a gene that allows for selection of bacterial cells that have replaced a native pMUT1 plasmid with a pMUT1 plasmid comprising a heterologous nucleic acid described herein. For example, the pMUT1 plasmid may be genetically modified with a gene that confers transfected bacterial antibiotic resistance. In some embodiments, the pMUT1 plasmid comprises an antibiotic resistance gene. For example, in some embodiments, the pMUT1 plasmid comprises a chloramphenicol resistance gene. In some embodiments, the chloramphenicol resistance gene is $Chl^R$. In some embodiments, the pMUT1 plasmid comprises a kanamycin resistance gene. In some embodiments, the pMUT1 plasmic comprises a streptomycin resistance gene. In some embodiments, the pMUT1 plasmid comprises a carbenicillin resistance gene. In some embodiments, the pMUT1 plasmid comprises a tolC gene which encodes the outer membrane protein TolC that confers resistance to toxic small molecules.

In some embodiments, the pMUT2 plasmid is genetically modified to comprise a gene that allows for selection of bacterial cells that have replaced a native pMUT2 plasmid with a pMUT2 comprising a heterologous nucleic acid described herein. For example, the pMUT2 plasmid may be genetically modified with a gene that confers transfected bacterial antibiotic resistance. In some embodiments, the pMUT2 plasmid comprises an antibiotic resistance gene. For example, in some embodiments, the pMUT2 plasmid comprises a chloramphenicol resistance gene. In some embodiments, the chloramphenicol resistance gene is $Chl^R$. In some embodiments, the pMUT2 plasmid comprises a kanamycin resistance gene. In some embodiments, the pMUT2 plasmic comprises a streptomycin resistance gene. In some embodiments, the pMUT2 plasmid comprises a carbenicillin resistance gene. In some embodiments, the pMUT2 plasmid comprises a tolC gene which encodes the outer membrane protein TolC that confers resistance to toxic small molecules.

In some embodiments, the pMUT1 or the pMUT2 plasmid is genetically modified to comprise a gene encoding levansucrase, an enzyme that produces a toxic byproduct in the presence of sucrose. In some embodiments, the gene encoding levansucrase is sacB. In some embodiments, the gene encoding levansucrase is operably linked to an inducible promoter.

In some embodiments, the pMUT1 or the pMUT2 plasmid is genetically modified to comprise a nucleic acid encoding the mRNA interferase toxin RelE (i.e., relE).

In one aspect, provided herein is a method for obtaining bacterial transfectants comprising an engineered pMUT1 or pMUT2 plasmid described herein. The inventors have surprisingly discovered that an engineered bacterial cell (e.g., *E. coli* Nissle) comprising either a first pMUT1 or a first pMUT2 plasmid, wherein the first pMUT1 or first pMUT2 plasmid comprises both a gene encoding levansucrase (e.g., sacB) and a first antibiotic resistance gene that confers resistance to a first antibiotic, can be used as a host cell for transfection in a negative selection process to readily obtain transfectants comprising an engineered pMUT1 or pMUT2 plasmid having a heterologous nucleic acid described herein. This engineered bacterial cell may be transfected with a second pMUT1 or a second pMUT2 plasmid, respectively, each comprising a heterologous nucleic acid described herein and a second antibiotic resistance gene that confers resistance to a second antibiotic. Once transfected, the bacterial strain is cultured (e.g., plated) on media comprising sucrose and the second antibiotic, thereby selecting for transfectants that have lost the first pMUT1 plasmid or the second pMUT2 plasmid (which comprise the gene encoding levansucrase and the first antibiotic resistance gene). This method allows for the generation of transfectants comprising either the second pMUT1 plasmid or the second pMUT2 plasmid without the need for a prolonged serial negative selection process that may sometimes require a prolonged period of time (up to several weeks).

In some embodiments, the pMUT1 or the pMUT2 plasmid is genetically modified to comprise a nucleic acid encoding a detectable marker such that transfected bacterial cells may be detected in vitro and/or in vivo. For example, in some embodiments, the PMUT1 or the pMUT2 plasmid is genetically modified to comprise a fluorescent protein (e.g., red fluorescent protein (RFP), green fluorescent protein (GFP), yellow fluorescent protein (YFP)).

In some embodiments, the pMUT1 or the pMUT2 plasmid is genetically modified to comprise nucleic acid encoding a near infrared fluorescent protein. Any near infrared fluorescent proteins may be used as described herein, and are described for example in Shcherbakova and Verkhusha (2013) *Nat. Methods* 10(8):751-4, the entire contents of which are incorporated herein by reference. In some embodiments the near infrared fluorescent protein is iRFP720. In some embodiments, the nucleic acid sequence encodes a near infrared fluorescent protein comprising the amino acid sequence of SEQ ID NO: 23, provided below. In some embodiments, the nucleic acid sequence encodes a near infrared fluorescent protein having at least 80% homology to SEQ ID NO: 23 (e.g., 80% or greater homology, 85% or greater homology, 90% or greater homology, or 95% or greater homology). In some embodiments, the nucleic acid sequence encodes a near infrared fluorescent protein having at least 80% identity to SEQ ID NO: 23 (e.g., 80% or greater identity, 85% or greater identity, 90% or greater identity, or 95% or greater identity).

Amino acid sequence of near infrared fluorescent protein iRFP720:

```
                                        (SEQ ID NO: 23)
MAEGSVARQPDLLTCDDEPIHIPGAIQPHGLLLALAADMTIVAGSDNLPE

LTGLAIGALIGRSAADVFDSETHNRLTIALAEPGAAVGAPITVGFTMRKD

AGFIGSWHRHDQLIFLELEPPQRDVAEPQAFFRRTNSAIRRLQAAETLES

ACAAAAQEVRKITGFDRVMIYRFASDFSGSVIAEDRCAEVESKLGLHYPA

SFIPAQARRLYTINPVRIIPDINYRPVPVTPDLNPVTGRPIDLSFAILRS

VSPNHLEFMRNIGMHGTMSISILRGERLWGLIVCHHRTPYYVDLDGRQAC

ELVAQVLAWQIGVMEE
```

In some embodiments, the nucleic acid sequence encoding the near infrared fluorescent protein is codon-optimized for expression in *E. coli*. For example, in some embodiments, the nucleic acid sequence encoding the near infrared fluorescent protein iRFP720 comprises the nucleic acid sequence of SEQ ID NO: 24, provided below.

Nucleic acid sequence encoding near infrared fluorescent protein iRFP720 codon-optimized for expression in *E. coli*:

```
                                        (SEQ ID NO: 24)
ATGGCTGAAGGAAGCGTCGCACGGCAGCCGGATTTACTGACGTGTGACGA

CGAACCCATACACATACCTGGTGCTATACAGCCACACGGTTTACTTCTGG

CTTTAGCTGCGGATATGACCATAGTCGCTGGTAGTGATAACCTGCCCGAA

TTGACGGGCTTGGCGATAGGAGCCCTTATTGGCCGGAGTGCAGCGGACGT

GTTTGATTCTGAAACACACAACCGTTTAACGATTGCGCTTGCAGAACCAG

GAGCCGCCGTTGGTGCCCCAATCACCGTCGGCTTCACCATGAGAAAGGAC

GCTGGCTTCATCGGTTCATGGCACAGACATGACCAGTTGATATTTTTAGA

ATTGGAGCCGCCACAGAGAGACGTAGCAGAGCCTCAGGCTTTTTTTCGGC

GGACGAACTCAGCTATCAGACGCTTACAGGCAGCTGAAACCTTGGAAAGC

GCATGTGCTGCCGCCGCTCAGGAGGTCCGTAAGATAACAGGGTTCGACAG

AGTGATGATTTATCGTTTTGCTTCGGATTTCTCCGGGTCGGTAATAGCAG

AAGACCGTTGTGCAGAAGTTGAAAGTAAACTGGGTCTTCATTACCCGGCA

TCTTTCATACCGGCACAAGCGCGTCGCTTATATACTATAAACCCTGTTCG

CATTATTCCAGACATCAATTACAGACCTGTACCTGTAACACCCGATCTTA

ACCCAGTAACGGGTCGTCCCATCGATTTGTCCTTCGCGATCTTAAGAAGC

GTTTCGCCTAATCACCTTGAGTTCATGCGGAATATCGGCATGCATGGTAC

CATGAGCATCAGCATTCTGCGCGGCGAGAGACTTTGGGGTTTGATCGTGT

GCCATCATCGGACCCCGTATTATGTAGACTTAGACGGTCGGCAAGCCTGC

GAGTTAGTGGCCCAAGTATTGGCATGGCAAATAGGTGTAATGGAGGAATA

A
```

In some embodiments the near infrared fluorescent protein is iRFP702. In some embodiments, the nucleic acid sequence encodes a near infrared fluorescent protein comprising the amino acid sequence of SEQ ID NO: 25, provided below. In some embodiments, the nucleic acid sequence encodes a near infrared fluorescent protein having at least 80% homology to SEQ ID NO: 25 (e.g., 80% or greater homology, 85% or greater homology, 90% or greater homology, or 95% or greater homology). In some embodiments, the nucleic acid sequence encodes a near infrared fluorescent protein having at least 80% identity to SEQ ID NO: 25 (e.g., 80% or greater identity, 85% or greater identity, 90% or greater identity, or 95% or greater identity).

Amino acid sequence of near infrared fluorescent protein iRFP702:

```
                                        (SEQ ID NO: 25)
MARKVDLTSCDREPIHIPGSIQPCGCLLACDAQAVRITRITENAGAFFGR

ETPRVGELLADYFGETEAHALRNALAQSSDPKRPALIFGWRDGLTGRTFD

ISLHRHDGTSIIEFEPAAAEQADNPLRLTRQIIARTKELKSLEEMAARVP

RYLQAMLGYHRVMLYRFADDGSGKVIGEAKRSDLESFLGQHFPASLVPQQ

ARLLYLKNAIRVVSDSRGISSRIVPEHDASGAALDLSFAHLRSISPIHLE

FLRNMGVSASMSLSIIIDGTLWGLIICHHYEPRAVPMAQRVAAEMFADFL

SLHFTAAHHQR
```

In some embodiments, the nucleic acid sequence encoding the near infrared fluorescent protein is codon-optimized for expression in *E. coli*. For example, in some embodiments, the nucleic acid sequence encoding the near infrared fluorescent protein iRFP702 comprises the nucleic acid sequence of SEQ ID NO: 26, provided below.

Nucleic acid sequence encoding near infrared fluorescent protein iRFP702 codon-optimized for expression in *E. coli*:

```
                                        (SEQ ID NO: 26)
ATGGCTCGGAAAGTAGACCTGACATCTTGTGACCGTGAGCCAATACACAT

CCCAGGGTCGATACAACCCTGTGGGTGCCTTCTTGCATGTGACGCACAAG

CCGTCCGGATAACTCGGATAACGGAAAACGCCGGTGCCTTTTTTGGAAGA
```

-continued

```
GAGACCCCTCGCGTTGGTGAACTTCTGGCAGATTACTTTGGAGAGACGGA

AGCCCATGCATTGAGAAATGCACTGGCCCAGTCATCCGACCCCAAAAGAC

CTGCGCTTATATTTGGCTGGCGGGATGGCCTTACAGGCCGTACGTTCGAT

ATATCCCTGCATAGACATGATGGTACAAGTATAATCGAGTTCGAACCGGC

GGCGGCAGAACAGGCAGACAATCCATTACGCCTTACTCGGCAGATTATAG

CCCGGACGAAAGAGTTAAAAAGTCTTGAGGAGATGGCAGCGAGAGTGCCG

AGATATTTGCAAGCAATGTTGGGATACCACCGGGTGATGCTTTATAGATT

CGCCGACGATGGGTCGGGTAAGGTGATCGGTGAAGCTAAAAGAAGTGATT

TAGAGTCCTTTCTGGGCCAGCATTTTCCAGCTTCCCTGGTTCCTCAGCAA

GCCCGCTTGCTGTATTTGAAAAATGCAATCCGCGTAGTATCAGACAGCCG

TGGTATATCCTCACGGATAGTACCGGAGCATGATGCTTCTGGAGCTGCTC

TGGATTTATCCTTTGCACATCTTCGCAGCATAAGTCCTATCCATTTAGAG

TTTTTGAGAAACATGGGGGTGTCGGCATCCATGTCGTTATCCATAATAAT

TGACGGCACACTGTGGGGGCTTATTATTTGTCATCATTACGAGCCGAGAG

CAGTTCCAATGGCACAACGCGTAGCTGCAGAAATGTTCGCTGATTTCTTG

TCTCTGCACTTCACTGCAGCACATCACCAGCGCTAA
```

In some embodiments, the nucleic acid encoding the detectable marker (e.g., a fluorescent protein) is under the control of a constitutive promoter. In some embodiments, the nucleic acid encoding the detectable marker (e.g., a fluorescent protein) is under the control of an inducible promoter. For example, in some embodiments, the nucleic acid encoding the detectable marker (e.g., a fluorescent protein) is under the control of an arabinose inducible promoter. In some embodiments, the pMUT1 or the pMUT2 plasmid is genetically modified to comprise one or more nucleic acid sequences of an inducible promoter system. For example, in some embodiments, the pMUT1 or the pMUT2 plasmid is genetically modified to comprise a first nucleic acid encoding the AraC protein (i.e., AraC) and a second nucleic acid on the plasmid is under the control of a promoter regulated by AraC (e.g, $P_{BAD}$ or $P_C$. In some embodiments, the pMUT1 or the pMUT2 plasmid is genetically modified to comprise a heterologous nucleic acid encoding a curli accessory protein required for protein secretion. In some embodiments, the pMUT1 or the pMUT2 plasmid is genetically modified to comprise a heterologous nucleic acid encoding CsgE (i.e., the csgE gene). In some embodiments, the pMUT1 or the pMUT2 plasmid is genetically modified to comprise a heterologous nucleic acid encoding CsgG (i.e., the csgG gene). In some embodiments, the pMUT1 or the pMUT2 plasmid is genetically modified to comprise a heterologous nucleic acid encoding both CsgE and CsgG.

Additional vectors (also referred to as "plasmids" herein) useful for transferring genes into bacterial cells are available. The plasmids may be episomal or may be integrated into the bacterial cell's genome through homologous recombination or random integration. In some embodiments, is an expression vector. A plasmid can be viral or non-viral. Plasmids for use as described herein can include, but are not limited to, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif, which is hereby incorporated by reference), pQE, pIH821, pGEX, pET series (see Studier et al. (1990) "Use of T7 RNA Polymerase to Direct Expression of Cloned Genes," Gene Expression Technology 185, which is hereby incorporated by reference in its entirety).

The expression of any of the genes incorporated into the engineered bacterium described herein may be regulated using any promoter known in the art. In some embodiments, the heterologous nucleic acid described herein is operably-linked to a promoter. In some embodiments, the promoter is a constitutive promoter. In some embodiments, a heterologous nucleic acid described herein is operably linked to a constitutive promoter and a ribosomal binding site. In some embodiments, a heterologous nucleic acid described herein is operably linked to an exemplary constitutive promoter and ribosomal binding site (RBS) provided in Table 3.

TABLE 3

Exemplary Constitutive Promoter/Ribosomal Binding Site Nucleic Acid Sequences

| Promoter-Ribosomal Binding Site | Nucleic Acid Sequence (* = location of start codon) |
|---|---|
| Constitutive-Promoter-RBS-1 | ggctacatcattcacttttcttcacaaccggtccctatcagtg atagagattgacatccctatcagtgatagagatactgagcac TCTAGAGTCACACAGGAAAGTACTA G * (SEQ ID NO: 30) |
| Constitutive-Promoter-RBS-2 | ggctacatcattcacttttcttcacaaccggtccctatcagtg atagagattgacatccctatcagtgatagagatactgagcac TCTAGAGATTAAAGAGGAGAAATAC TAG* (SEQ ID NO: 31) |
| Constitutive-Promoter-RBS-3 | ggctacatcattcacttttcttcacaaccggtttacggctagc tcagtcctaggtacaatgctagcTCTAGAGTCACA CAGGAAAGTACTAG* (SEQ ID NO: 32) |
| Constitutive-Promoter-RBS-4 | ggctacatcattcacttttcttcacaaccggtttacggctagc tcagtcctaggtacaatgctagcTCTAGAGATTAA AGAGGAGAAATACTAG* (SEQ ID NO: 33) |

In some embodiments, the promoter is an inducible promoter. An "inducible promoter" may be one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, tetracycline-inducible promoter, the lambda phage pL promoter, steroid-responsive promoters, rapamycin responsive promoters and the like. Inducible promoters for use in prokaryotic systems are well known in the art, see, e.g. the β-lactamase and lactose promoter systems (Chang et al. (1978) *Nature* 275: 615, which is incorporated herein by reference; Goeddel et al. (1979) *Nature* 281: 544, which is incorporated herein by reference), the arabinose promoter system, including the araBAD promoter (Guzman et al. (1992) *J. Bacteriol.* 174: 7716-28, which is incorporated herein by reference; Guzman et al. (1995) *J. Bacteriol.*, 177: 4121-30, which is incorporated herein by reference; Siegele and Hu (1997) *Proc. Natl. Acad. Sci. USA* 94: 8168-72, which is incorporated herein by reference), the rhamnose promoter (Haldimann et al. (1998) *J. Bacteriol.* 180: 1277-86, which is incorporated herein by reference), the alkaline phosphatase promoter, a tryptophan (trp) promoter system (Goeddel (1980) *Nucleic Acids Res.*, 8: 4057, which is incorporated herein by reference), the PLtetO-1 and Plac/are-1 promoters (Lutz and Bujard (1997) *Nucleic Acids Res.* 25: 1203-10, which is incorporated herein by reference), the phage lambda pL promoter system and pR promoter system (Simmons et al. (1984) *Gene* 28(1): 55-64; Gilman and Love (2016) *Biochem. Soc. Trans.* 44(3): 731-7; and Valdez-Cruz et al. (2010) *Microb. Cell Fact.* 9: 18. which are incorporated herein by reference), and hybrid promoters such as the tac promoter (see deBoer et al. (1983) *Proc. Natl. Acad. Sci. USA* 80: 21-5, which is incorporated herein by reference).

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including $Cu^{2+}$, $Ca^{2+}$, and $Zn^{2+}$), galactose, arabinose, anhydrotetracycline (ATc), tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present bacteria are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline, or the tetracycline analog anhydrotetracycline (ATc), will cause the dissociation of the tet repressor from the engineered promoter and allow transcription of the sequence downstream of the engineered promoter to occur.

In one aspect, the technology described herein relates to libraries of therapeutic polypeptides and/or peptides which can be screened and/or tested for therapeutic and/or biological activity. In some embodiments, described herein is a library of a plurality of heterologous nucleic acid sequences (e.g., the heterologous nucleic acid sequence described herein) encoding heterologous polypeptide sequences, the library comprising: a plurality of clonal prokaryotic cell populations; wherein each clonal population is comprised of prokaryotic cells as described herein; and wherein the clonal populations collectively comprise a plurality of nucleic acid sequences encoding heterologous polypeptide sequences. In some embodiments, described herein is a library of a plurality of heterologous polypeptide sequences, the library comprising: a plurality of populations of heterologous polypeptides encoded by a heterologous nucleic acid described herein; wherein each population of heterologous polypeptides is obtained according to the methods described herein. In some embodiments, each population can comprise a unique heterologous nucleic acid sequence.

Methods of creating bacterial libraries, and/or libraries of compounds isolated from bacterial cells are well known in the art. By way of non-limiting example, a bacterial cell library can be in the form of a plurality of multi-well plates, with each well of a plate comprising a clonal bacterial population. The clonal bacterial populations can be provided in media (e.g., solid media or liquid media) or in glycerol stocks. In some embodiments, a library can comprise multiple wells which comprise identical clonal populations, i.e. a clonal population can appear multiple times in a library. In some embodiments, a library can comprise a plurality of multi-well plates, with each well of a plate comprising one or more heterologous polypeptide sequences isolated from one or more clonal bacterial populations. Methods of isolating polypeptides from bacterial cells are well known in the art and examples are described elsewhere herein. In some embodiments, libraries can be created using automated and/or high-throughput methods, e.g., robotic colony-picking.

In some embodiments, a library can comprise pooled samples, e.g., multiple clonal bacterial populations, multiple isolated heterologous polypeptides, or multiple isolated populations of heterologous polypeptides can be pooled so that a smaller number of samples must be initially screened. The individual components of a "positive" pool can be subsequently screened separately. In some embodiments, a pool can comprise as many as 30 clonal populations, e.g., 2 or more clonal populations, 10 or more clonal populations, 20 or more clonal populations, or 30 or more clonal populations. In some embodiments, a pool can comprise as many as 24 clonal populations.

In some embodiments, a library can comprise 10 or more pools of, populations of, and/or individual heterologous polypeptide species (e.g., isolated or present within bacterial cells), e.g., 10 or more, 100 or more, 1,000 or more, 10,000 or more, or 100,000 or more pools of, populations of, and/or individual heterologous polypeptide species.

Bacteria for use in the methods and compositions described herein can be of any species. Preferably, the bacteria are of a species and/or strain which is amenable to culture and genetic manipulation. In some embodiments, the bacterium is a Gram-negative bacterium. In some embodiments, the bacterium is a probiotic. In some embodiments, the bacterium is Generally Recognized as Safe (GRAS) by a regulatory authority. In some embodiments, the bacterium is pathogenic. In some embodiments, the bacterium is non-pathogenic. In some embodiments, the bacterium is an attenuated pathogenic bacterium. In some embodiments, the parental strain of the bacterium used herein is of a strain optimized for protein expression.

Non-limiting examples of bacterial species and strains suitable for use in the present technologies include *Escherichia coli, E. coli* BL21, *E. coli* Tuner, *E. coli* Rosetta, *E. coli* JM101, and derivatives of any of the foregoing. In one embodiment, the bacterium is of the *E. coli* Nissle 1917 strain. In one embodiment, the bacterium is *E. coli* W strain (ATCC 9637). Other non-pathogenic bacterial strains known to those of skill in the art such as MG1655, K12-derived strains (e.g., W3110), and the like, may also be used.

In some embodiments, the bacterium has been genetically-modified to comprise a heterologous csgE gene (which encodes CsgE). In some embodiments, the heterologous csgE gene is an *E. coli* csgE gene. In some embodiments, the bacterium has been genetically-engineered to comprise a heterologous csgG gene. In some embodiments, the heterologous csgG gene is an *E. coli* csgG gene (which encodes (CsgG). In some embodiments, the bacterium has been genetically-modified to comprise a heterologous csgE gene and a heterologous csgG gene.

In some embodiments, the bacterium has been genetically-modified to comprise a heterologous ffh gene (which encodes Ffh protein). In some embodiments, the bacterium has been genetically-modified to comprise a heterologous ftsY gene (which encodes the Signal recognition particle receptor protein FtsY. In some embodiments, the bacterium has been genetically engineered to comprise a heterologous ffs gene (which encodes 4.5S RNA). In some embodiments, the bacterium has been genetically-modified to comprise one or more of a heterologous ffh gene, a heterologous ftsY gene, and a heterologous ffs gene.

In some embodiments, the bacterium has been genetically-modified to comprise one or more of a heterologous ffh gene, a heterologous ftsY gene, and a heterologous ffs gene, and one or more of a heterologous csgE gene and a heterologous csgG gene.

In some embodiments, the bacterium comprises a native csgE gene. In one embodiment, the bacterium comprises a native csgG gene. In one embodiment, the bacterium comprises a native ffh gene. In some embodiments, the bacterium comprises a native ftsY gene. In some embodiments, the bacterium comprises a native ffs gene.

In some embodiments, the bacterium comprises a genetic modification in a csgA gene or a csgB gene. In some embodiments, the genetic modification is a point mutation, a partial deletion, or a knockout of the gene. In some embodiments, the bacterium does not transcribe or translate an mRNA encoding CsgA. In some embodiments, the bacterium does not express CsgA. In some embodiments, the bacterium does not transcribe or translate an mRNA encoding CsgB. In some embodiments, the bacterium does not express CsgB.

Pharmaceutical Compositions

Pharmaceutical compositions comprising the engineered bacterium described herein may be used to diagnose, treat, manage, ameliorate, and/or prevent a disease or disorder, as described herein. Pharmaceutical compositions comprising one or more engineered bacteria, alone or in combination with prophylactic agents, therapeutic agents, and/or pharmaceutically acceptable carriers are provided.

In certain embodiments, the pharmaceutical composition comprises one species, strain, or subtype of bacteria that are engineered to comprise the genetic modifications described herein, e.g., to express a therapeutic polypeptide. In alternate embodiments, the pharmaceutical composition comprises two or more species, strains, and/or subtypes of bacteria that are each engineered to comprise the genetic modifications described herein, e.g., to express at least one therapeutic polypeptide.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tableting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{12}$ bacteria. The composition may be administered once or more daily, weekly, or monthly.

The engineered bacterium may be formulated into pharmaceutical compositions comprising one or more pharmaceutically acceptable carriers, thickeners, diluents, buffers, buffering agents, surface active agents, neutral or cationic lipids, lipid complexes, nanoparticles, liposomes, penetration enhancers, carrier compounds, and other pharmaceutically acceptable carriers or agents. Further, any one of the detectable compound, inducer, and/or nonstandard amino acid may also be formulated into pharmaceutical compositions comprising one or more pharmaceutically acceptable carriers, thickeners, diluents, buffers, buffering agents, surface active agents, neutral or cationic lipids, lipid complexes, nanoparticles, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. The engineered bacterium may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. The engineered bacterium disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art.

The pharmaceutical compositions disclosed herein may be administered orally and formulated as tablets, pills, capsules, lozenges, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the pharmaceutical compositions may be enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the engineered bacterium described herein.

In some embodiments, the pharmaceutical composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The pharmaceutical compositions described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The pharmaceutical compositions may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, lozenge, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Methods

In some embodiments, disclosed herein are methods for treating a disease or disorder in a subject. In some embodiments, the method comprises administering to a subject an engineered bacterium described herein. In some embodiments, the engineered bacterium comprises a heterologous nucleic acid, wherein the nucleic acid comprises a nucleic acid sequence encoding a signal recognition particle (SRP) pathway signal sequence, a nucleic acid sequence encoding a CsgGE export signal sequence, and a nucleic acid sequence encoding a therapeutic polypeptide. In some embodiments, the engineered bacterium comprises a heterologous nucleic acid, wherein the nucleic acid comprises a nucleic acid sequence encoding a SecA-dependent secretion signal, a nucleic acid sequence encoding a CsgGE export signal sequence, and a nucleic acid sequence encoding a therapeutic polypeptide. In one embodiment, the engineered bacteria described herein may be administered to a subject, colonize the subject (e.g., the subject's gut), and secrete a therapeutic polypeptide of interest in an effective amount to treat a disease or disorder in a subject in need thereof.

In some embodiments, the plasmid comprises a selectable marker gene (e.g., a selectable marker gene that expresses a protein that confers the engineered bacterium resistance to an antibiotic). In some embodiments, the heterologous nucleic acid is located on a plasmid that lacks a selectable marker gene. In some embodiments, the heterologous nucleic acid is located on a pMUT1 or pMUT2 plasmid.

The engineered bacterium administered to the subject may be engineered to express any therapeutic polypeptide of interest. In some embodiments, the therapeutic protein is an antibody, an antibody fragment, an enzyme, a fusion protein, a hormone, an antigen, a thrombolytic agent, a cytokine, or a growth factor. In some embodiments, the therapeutic protein is an antibody. In some embodiments, the therapeutic protein is a single domain antibody. The engineered bacterium described herein are particularly suitable for the expression of therapeutic polypeptides comprising a stabilizing disulfide bond (e.g., an antibody or an antibody fragment, such as a single domain antibody) because SRP-mediated translocation of the nascent protein into the bacterial periplasm as it is being translated allows for proper protein folding to occur under the oxidizing conditions of the bacterial periplasm. Thus, the therapeutic polypeptides can be expressed in vivo in the proper conformation.

In some embodiments, the engineered bacterium is non-pathogenic. In some embodiments, the engineered bacterium is a probiotic. In some embodiments, the engineered bacterium is a Gram-negative bacterium.

The delivery of therapeutic proteins directly to the site of action (e.g., the gut) may be particularly advantageous in effectively targeting some diseases or disorders. Thus, for example, in a subject suffering from a gastrointestinal disease or disorder, the engineered bacteria described herein may be used for the targeted delivery of a therapeutic protein to the gut. In some embodiments, the therapeutic protein is an antibody. In some embodiments, the therapeutic protein is a single-domain antibody. In some embodiments, the single domain antibody is specific for an antigen of interest. In some embodiments, the antigen is a tumor antigen, an infectious agent antigen (e.g., a bacterial antigen, a viral antigen, a prion antigen, or a parasite antigen), a autoimmune antigen, a tumor antigen, an antigen of the host subject, a toxin, a poison, an inflammatory compound, a chemical compound, a heavy metal, an allergenic molecule, an endogenous hormone, a signaling molecule, a dietary component, or a metabolite. In some embodiments, the antigen is carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, or *Plasmodium* membrane protein.

In some embodiments, the disease or disorder is a gastrointestinal disease or disorder. In some embodiments the gastrointestinal disease or disorder is inflammatory bowel disease, Crohn's disease, ulcerative colitis, colorectal cancer, ulcer, malabsorption, short-gut syndrome, cul-de-sac syndrome, celiac sprue, tropical sprue, hypogammaglobulinemic sprue, gastroesophageal reflux disease, enteritis, dyspepsia, functional dyspepsia, non-ulcer dyspepsia, gastroparesis, chronic intestinal pseudo-obstruction, short bowel syndrome, and gastrointestinal cancer. In some embodiments, the disease or disorder is a systemic disease or disorder. In some embodiments, the disease or disorder is a respiratory disease or disorder. In some embodiments, the disease or disorder is an autoimmune disease or disorder. In some embodiments, the disease is an infectious disease. In some embodiments, the disease or disorder is a proliferative disease or disorder. In some embodiments, the disease or disorder is cancer. In some embodiments, the disease or disorder is a precancerous lesion. In some embodiments, the disease or disorder is an inflammatory disease or disorder. In some embodiments, the disease or disorder is an allergy, asthma, rheumatoid arthritis, diabetes, lupus, a viral infection (e.g., an HIV infection, a rotavirus infection, a norovirus infection, an astrovirus infection, or an enteric adenovirus infection), multiple sclerosis, cystic fibrosis, a viral infection, a bacterial infection (e.g., an infection with *Vibrio cholera, Cryptosporidium, Clostridium botulinum, Campylobacter, Salmonella, Shigella*, pathogenic *Escherichia coli*, etc.), a protozoal infection (e.g., malaria), a fungal infection, or a parasitic infection (e.g., an infection with *Giardia lamblia, Enterobius vermicularis, Ancylostoma duodenale, Necator americanus, Entamoeba histolytica, Cryptosporidium* sp., *Giardia intestinalis (lamblia), Cystoisospora (Isospora) belli, Cyclospora cayetanensis*, and members of the phylum Microsporidia roundworms, tapeworms, pinworms, whipworms, hookworms, a congenital genetic disorder, a tissue or organ trauma, toxin ingestion, heavy metal poisoning, aging, or a metabolic disorder.

In some embodiments, the subject is an animal. In some embodiments, the subject is a mammal. In some embodiments, the subject is a domesticated animal. In some embodiments, the subject is a ruminant. In some embodiments, the subject is a non-human mammal. In some embodiments, the subject is a human subject.

The methods described herein may comprise preparing a pharmaceutical composition with at least one genetically engineered species, strain, or subtype of bacteria described herein, and administering the pharmaceutical composition to a subject in a therapeutically effective amount. In some embodiments, the engineered bacteria disclosed herein are administered orally, e.g., in a liquid suspension. In some embodiments, the engineered bacteria are lyophilized in a gel cap and administered orally. In some embodiments, the engineered bacteria are administered via a feeding tube or gastric shunt. In some embodiments, the engineered bacteria are administered rectally, e.g., by enema. In some embodiments, the engineered bacteria are administered topically, intraintestinally, intrajejunally, intraduodenally, intraileally, and/or intracolically.

The methods disclosed herein may comprise administering a pharmaceutical composition comprising engineered bacteria alone or in combination with one or more additional therapies, e.g., chemotherapy. The pharmaceutical composition may be administered alone or in combination with one or more additional therapeutic agents. An important consideration in the selection of the one or more additional therapeutic agents is that the agent(s) should be compatible with the bacteria, e.g., the agent(s) must not interfere with or kill the bacteria.

In some embodiments, the engineered bacterium described herein, or pharmaceutical compositions comprising the engineered bacterium described herein may be administered to a subject, and a period of time is allowed to lapse in order to allow the bacterium to engraft and/or colonize in the subject (e.g., in the subject's gastrointestinal tract, skin and/or respiratory tract). Thereafter, any intervention using the methods described herein may be used.

In some embodiments, it may be necessary to administer an agent (i.e., an inducer) that regulates one or more inducible promoter that regulate the expression of the heterologous gene being expressed by the engineered bacterium described herein. The inducer will activate the expression of the heterologous gene encoding the protein of interest. In some embodiments, the inducer is administered in a pharmaceutical composition. In some embodiments, the inducer is administered to the subject as part of a nutritional product. In some embodiment, the inducer is administered orally, intravenously, intradermally or rectally. In some embodiments, the inducer is administered to the subject at least one, two, three, four, five, six, eight, twelve, sixteen, twenty, twenty-four, thirty-six or forty-eight hours prior to administering a detectable compound or drug to the subject comprising a bioorthogonal reactive functional group. In some embodiments, the inducer is administered to the subject at least one, two, three, four, five, six, or seven days prior to administering a detectable compound or drug to the subject comprising a bioorthogonal reactive functional group.

In one aspect, described herein is a method of producing a recombinant polypeptide, comprising culturing an engineered bacterium under conditions suitable for the expression and export of the recombinant polypeptide from the engineered bacterium, wherein the recombinant polypeptide comprises a CsgGE export signal sequence and a therapeutic polypeptide. Such conditions can include, but are not limited to, conditions under which the engineered bacterium is capable of logarithmic growth and/or polypeptide synthesis. Conditions may vary depending upon the species and strain of bacteria selected. Conditions for the culture of bacteria are well known in the art. If the recombinant polypeptide is operatively linked to an inducible promoter, such conditions can include the presence of a suitable inducer(s) (e.g., arabinose or IPTG).

The engineered bacteria described herein are particularly advantageous for the expression of the recombinant polypeptides that are otherwise normally deleterious to the cell because by the SRP pathway signal sequence mediates the recombinant polypeptide transport to the bacterial periplasm as the polypeptide is translated, thus avoiding or reducing any deleterious effect that the recombinant polypeptide may induce in the bacterial cell cytoplasm and/or periplasm. Without wishing to be bound by any particular theory, the engineered bacteria described herein express and secrete recombinant polypeptides (e.g., therapeutic polypeptides) via a constant outflow which prevents the protein from accumulating in the cytoplasm and/or periplasm. Therefore, using the expression system described herein, the recombinant polypeptide can be readily expressed without inducing cellular toxicity, or inducing reduced cellular toxicity. Thus, in some embodiments, the recombinant polypeptide is not toxic to the engineered bacterium described herein. In some embodiments, the recombinant polypeptide has reduced toxicity to the engineered bacterium as compared to the level of toxicity of a recombinant polypeptide expressed from a heterologous nucleic acid sequence lacking the nucleic acid sequence encoding the SRP pathway signal sequence and/or lacking the nucleic acid sequence encoding the CsgGE export signal sequence under the same conditions.

The expression system described herein is advantageous because the formation of inclusion bodies and/or protein aggregates comprising the recombinant polypeptide may be reduced since the proteins are allowed to properly fold in the periplasm environment, avoiding the formation of misfolded proteins that form inclusion bodies and/or protein aggregates. Thus, in some embodiments, inclusion bodies comprising the recombinant polypeptide are not formed during expression and export of the recombinant polypeptide in the engineered bacterium. In some embodiments, the amount of inclusion bodies formed in the engineered bacterium is decreased by at least 1-fold as compared to the amount of inclusion bodies formed during expression of a recombinant polypeptide comprising the therapeutic polypeptide without the SRP pathway signal sequence and/or without the CsgGE export signal sequence in an engineered bacterium under the same conditions. In some embodiments, the amount of inclusion bodies formed in the engineered bacterium is decreased by at least 2-fold, 3-fold, 4-fold, or 5-fold, 6-fold, 7-fold, 8-fold, 9-fold, 10-fold, 15-fold, 20-fold, 30-fold, 40-fold, 50-fold, or more.

In some embodiments, protein aggregates comprising the recombinant polypeptide are not formed during or after expression and export of the recombinant polypeptide from the engineered bacterium. In some embodiments, the amount of protein aggregates formed is decreased by at least 1-fold as compared to the amount of protein aggregates formed during expression of a recombinant polypeptide comprising the therapeutic polypeptide without the SRP pathway signal sequence and/or without the CsgGE export signal sequence in an engineered bacterium under the same conditions. In some embodiments, the amount of protein aggregates formed is decreased by at least 2-fold, 3-fold, 4-fold, or 5-fold, 6-fold, 7-fold, 8-fold, 9-fold, 10-fold, 15-fold, 20-fold, 30-fold, 40-fold, 50-fold, or more.

In some embodiments, the level of expression and export of the recombinant polypeptide is increased by at least 2-fold, as compared to the level of expression and export of the recombinant polypeptide expressed from a heterologous nucleic acid sequence lacking the nucleic acid sequence encoding the SRP pathway signal sequence and/or lacking the nucleic acid sequence encoding the CsgGE export signal sequence, from an engineered bacterium under the same conditions. In some embodiments, the level of expression and export of the recombinant polypeptide is increased by at least 3-fold, 4-fold, 5-fold, 6-fold, 7-fold, 8-fold, 9-fold, 10-fold, 15-fold, 20-fold, 30-fold, 40-fold, 50-fold, or more.

In some embodiments, the methods of producing a recombinant polypeptide described herein further comprise collecting the recombinant polypeptide from cell culture medium comprising the engineered bacterium. In some embodiments, the engineered bacterium is not exposed to a lysing agent prior to collecting the recombinant protein from the cell culture medium. In some embodiments, the recombinant polypeptide is collected from a supernatant of the cell culture medium. Methods for collecting a recombinant polypeptide from a cell culture medium are well known in the art, and include, for example, filtration, centrifugation, dialysis, ultrafiltration, and lyophilization.

In some embodiments, the methods of producing a recombinant polypeptide described herein further comprise purifying the recombinant polypeptide. Recombinant polypeptides can also be isolated from cellular lysates and/or cell culture medium by using any standard technique known in the art. For example, recombinant polypeptides can be engineered to comprise an epitope tag such as a polyhistidine tag or other polypeptide tag such as myc or FLAG. Purification can be achieved by immunoprecipitation using antibodies specific to the recombinant peptide (or any epitope tag comprised in the amino sequence of the recombinant polypeptide) or by running the lysate solution or cell culture medium through an affinity column that comprises a matrix for the polypeptide or for any epitope tag comprised in the recombinant polypeptide (see for example, Ausubel et al., eds. (1993) Current Protocols in Molecular Biology, Section 10.11.8, John Wiley & Sons, New York).

Other methods for purifying a recombinant polypeptide include, but are not limited to ion exchange chromatography, hydroxylapatite chromatography, hydrophobic interaction chromatography, preparative isoelectric focusing chromatography, molecular sieve chromatography, HPLC, native gel electrophoresis in combination with gel elution, affinity chromatography, and preparative isoelectric. See, e.g., Marston et al. (1990) Meth. Enz., 182:264-275.

In another aspect, the present disclosure provides a recombinant polypeptide produced using the methods described herein. In some embodiments, the recombinant polypeptide comprises a signal recognition particle (SRP) pathway signal sequence, a CsgGE export signal sequence, and a therapeutic polypeptide. In some embodiments, the recombinant polypeptide further comprises a polypeptide tag described herein. In some embodiments, the recombinant polypeptide comprises a protease cleavage site amino acid sequence. In some embodiments, the CsgGE export signal sequence is N-terminal of the therapeutic polypeptide. In some embodiments, the SRP pathway signal sequence is N-terminal of the therapeutic polypeptide. In some embodiments, the CsgGE export signal sequence and the SRP pathway single sequence are N-terminal of the therapeutic polypeptide.

EXAMPLES

The following examples are set forth as being representative of the present disclosure. These examples are not to be construed as limiting the scope of the present disclosure as these and other equivalent embodiments will be apparent in view of the present disclosure, figures and accompanying claims.

Unless otherwise stated, the present methods were performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques, Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

Single-domain antibodies are small proteins approximately 15 kDa in size that are derived from llama, alpaca, camel, or shark antibodies and are able to bind with high affinity to a wide range of substrates. They are also referred to as nanobodies, intrabodies, or simply VHH domains. In contrast to canonical antibodies that are composed of two domains (heavy and light chains) that together define an antigen binding site, single domain antibodies possess a number of distinct advantages, including efficient folding, high solubility, extensive structural stability, increased tissue/tumor penetration due to the small size, recognition of epitopes inaccessible to typical antibodies, and binding affinities on par with typical antibodies (see, e.g., de Marco (2011)). Expression of single domain antibodies in E. coli, the major laboratory and industrial bacterial platform in use today, consists of expression of these proteins in the bacterial cytoplasm or periplasm, followed by cell lysis and protein purification. The high local concentration of recombinant single domain antibodies in the cell during overexpression may lead to formation of inclusion bodies, a common issue in the field of recombinant protein production. Such inclusion body formation is often toxic to the cell and limits total protein yield. Resolving functional single domain antibodies from inclusion bodies necessitates additional complex procedures beyond those undertaken during typical protein purification.

The novel methods described herein provide for the extracellular secretion of single domain antibodies, in part, by using the T8SS of E. coli. These methods result in the production of recombinant protein devoid of problems often encountered during recombinant protein expression by inducing the secretion of the single domain antibody to the extracellular space, a highly diluting environment that may prevent the formation of inclusion bodies. Efficient secretion of the protein also prevents intracellular buildup, eliminating cell toxicity problems. Further, purification of the recombinant polypeptide from the extracellular milieu, which contains very few proteins, is greatly simplified, a key consideration for the cost-effective production of these proteins for commercial use. This technology also enables the use of engineered bacteria expressing single domain antibodies for therapeutic and/or diagnostic applications in vivo, by using a probiotic (e.g., the non-pathogenic E. coli Nissle 1917).

Example 1: Generation of Engineered Bacteria Expressing Recombinant Polypeptides Comprising a SecA-Dependent Secretion Signal, a CsgGE Export Signal Sequence and Single-Domain Antibodies Engineered bacteria were generated by E. coli Nissle 1917 csgA knockout with a pBbA8c plasmids described below and in Table 4, each comprising a heterologous nucleic acid encoding single domain antibodies fused to a SecA-dependent secretion signal and an N22 leader sequence described below.

Briefly, the nucleic acid encoding the Sec-N22 leader sequence from E. coli strain MG1655 CsgA, an N-terminal sequence comprising a SecA-dependent secretion signal which mediates the translocation of the protein through the Sec translocon and into the bacterial periplasm, which is cleaved from the remaining N22 leader sequence in the bacterial periplasm by bacterial peptidases (e.g., peptidase I). The N22 leader sequence comprises a CsgGE export signal sequence that directs the polypeptide to the CsgG porin in a CsgE-dependent manner for extracellular secretion. The Sec-N22 leader sequence was fused to nucleic acid sequences encoding various single domain antibodies. The constructs were cloned into the plasmid pBbA8c, whereby the nucleic acid is operably linked to an arabinose-inducible promoter. Single domain antibodies binding to a variety of antigens and originally derived from different species were used. Table 4 lists the various plasmids that were generated, the antigen to which each single domain antibody is specific for, the animal from which each single domain antibody was originally derived, and a reference describing the single domain antibody (see, e.g., Ditlev et al. (2014); Doshi et al., (2014); Hussack et al. (2011); Koromyslova & Hansman (2015); Rothbauer et al. (2006); Saerens et al. (2005); Vaneycken et al. (2010); Vega et al. (2013); and Yang et al. (2014)).

TABLE 4

Plasmids used herein

| Name | Antigen | Derived From | Note | Reference |
|---|---|---|---|---|
| pBbA8c-Ctrl | None | — | Negative Control | — |
| pBbA8c-NbCEA5 | Carcinogenic Embryonic Antigen (CEA5) | Llama | Experimental | J. Nucl. Med. 51(7): 1099-106 (2010). |
| pBbA8c-NbGLUT1 | Glucose Transporter 1 (GLUT1) | Camelised human VH3 | Experimental | Sci. Rep. 4: 6760 (2014). |
| pBbA8c-NbGFP | Green Fluorescent Protein (GFP) | Llama | Experimental | Nat. Meth. 3: 887-889 (2006) |
| pBbA8c-Nb208 | Green Fluorescent Protein (GFP) | Llama | Experimental | WO 2015/097289 A1 |
| pBBA8c-NbUS | beta-Lactamase (cAbBCII10; universal scaffold) | Llama | Experimental | J. Mol. Biol. 352(3): 597-607 (2005). |
| pBbA8c-Nb5Ds | Clostridium difficile Toxin B (TcdB) | Alpaca | Experimental | J. Infect. Dis. 210(6): 964-72 (2014) |
| pBbA8c-NbAA6 | Clostridium difficile Toxin A (TcdA) | Alpaca | Experimental | J. Infect. Dis. 210(6): 964-72 (2014) |
| pBbA8c-DsbAss-NbAA6 | TcdA via SRP pathway | Alpaca | Experimental | — |
| pBbA8c-NbNoro85 | Norovirus Capsid | Alpaca | Experimental | J. Virol. 89(5): 2718-30 (2015). |
| pBbA8c-NbRota3B2 | Rotavirus Capsid | Llama | Experimental | PLoS Pathog. 9(5): e1003334 (2013) |

TABLE 4-continued

Plasmids used herein

| Name | Antigen | Derived From | Note | Reference |
|---|---|---|---|---|
| pBbA8c-NbTcdA-A26 | *Clostridium difficile* Toxin A (TcdA) | Llama | Experimental | *JBC* 286(11): 8961 (2011) |
| pBbA8C-NbVAR2CSA | *Plasmodium* membrane protein | Alpaca | Experimental | *PLoS One* 9(1): e84981 (2014) |

Cells were cultured at 25° C. in low salt (YESCA) media, comprising 1 g/L of yeast extract and 10 g/L of casamino acids. The media was supplemented with 34 micrograms/mL of chloramphenicol. Expression cultures were inoculated with starter cultures using the conditions described above. After growth to mid-log phase, the expression cultures were induced with 0.1-1 mM of arabinose. After 24-48 hours of growth, the subcellular fractions of the cells were isolated using the following procedures:

Isolation of the Periplasmic and Cytoplasmic Cellular Fractions—

Cultures were placed on ice. 0.5 mL of the culture were placed into a 2 mL microcentrifuge tube, on ice. Cells were pelleted by centrifuging (3,500 rpm, 5 min, 4° C.). Cell pellets were gently washed by resuspension in 1 mL of 1×TBS, and pelleted again as described above. Cell pellets were resuspended in 100 µL of ice-cold sucrose buffer (50 mM Tris; 1 mM EDTA; 20% sucrose), and incubated at 4° C. with gentle shaking for 10 min. Cells were pelleted again via centrifugation (4,000×g, 10 min, 4° C.). Cell pellets were resuspended in 100 µL of ice-cold 5 mM $MgCl_2$, and incubated at 4° C. with gentle shaking for 10 min. Cells were pelleted again via centrifugation (4,000×g, 15 min, 4° C.), and supernatants saved (periplasmic fraction). Pellets were washed by gently adding 100 µL of ice-cold 5 mM $MgCl_2$, and spun at (4,000×g, 5 min., 4° C.), and resuspended in 200 µL of 1×TBS (cytoplasmic fraction).

Isolation of Secreted Proteins—

9 mL of cooled culture was centrifuged at 3,500 rpm, 30 min., 4° C. Supernatant were filtered using a 0.22 micron syringe filter and a 10 mL syringe. 300 µl of QIAGEN NiNTA resin slurry were added to the supernatant and incubated for at least 1 hour or overnight with gentle shaking at 4° C. Resin was spun down (by centrifugation at 2000×g, 10 min., 4° C.). Media was carefully removed without disturbing the resin. 10 mL of His Wash Buffer (25 mM Tris, 300 mM NaCl, 0.05% Tween-20, 1% glycerol, 10 mM imidazole) was mix-in with the resin and incubated for 15 minutes with gentle shaking at 4° C. Resin was spun down (by centrifugation at 2000×g, 10 min., 4° C.), and the wash buffer was removed without disturbing the resin. The washed resin was gently resuspended in 1 mL of wash buffer and added to a mini spin column. Wash buffer was removed by briefly centrifuging the spin column. 100 µL of His Elution Buffer (25 mM Tris, 300 mM NaCl, 0.05% Tween-20, 1% glycerol, and 400 mM imidazole) was added to the spin column and the column was incubated at room temperature for 10 minutes, and then spun to elute the protein.

Figure 3:
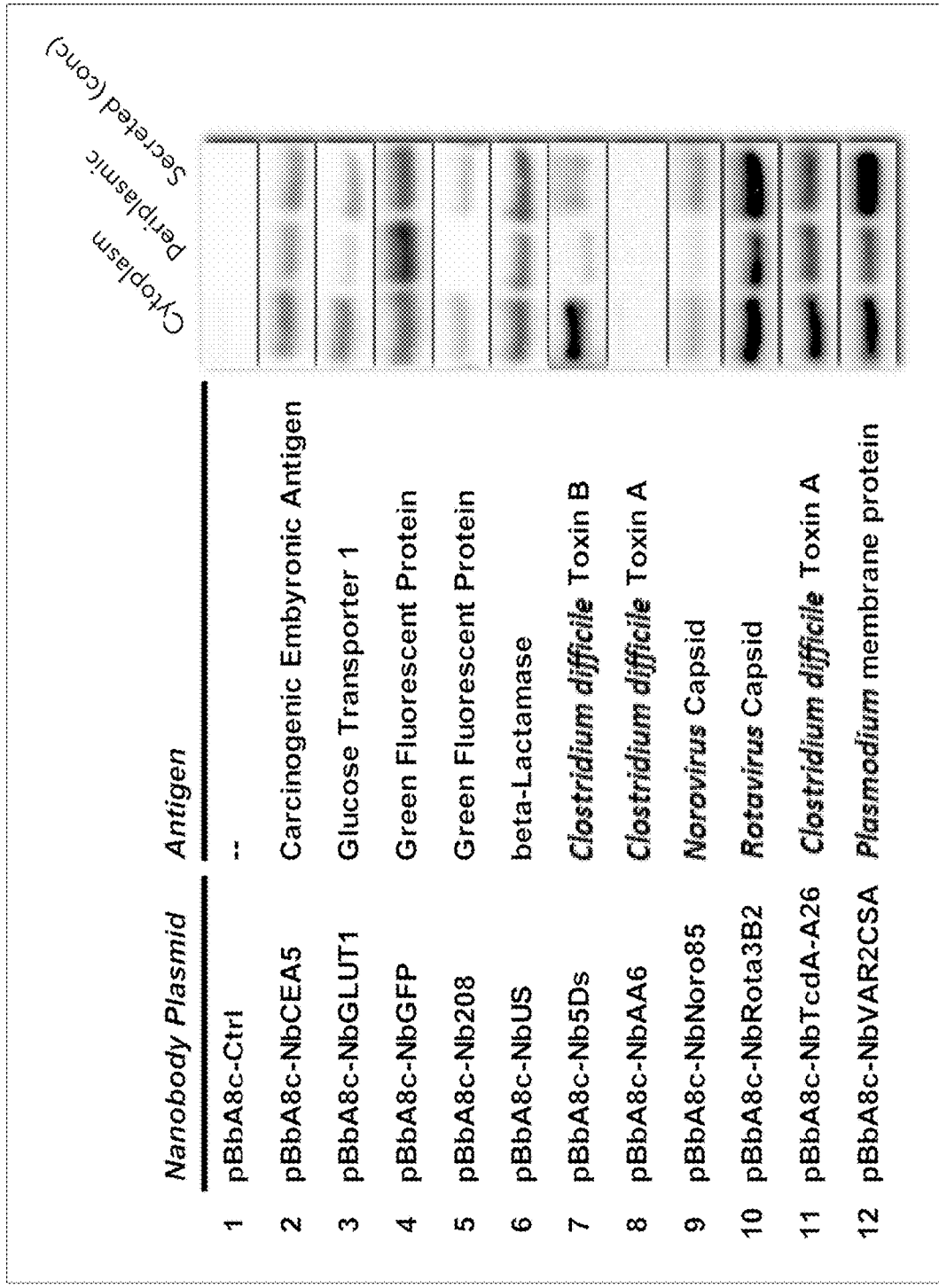
FIG. 3 shows an SDS-PAGE of subcellular fractions derived from *E. coli* Nissle 1917 expressing a heterologous nucleic acid encoding the native 42-amino acid Sec-N22 leader sequence from *E. coli* CsgA fused to one of 11 different single domain antibodies specific for the antigens: (1) control; (2) carcinogenic embryonic antigen (CEA); (3) glucose transporter 1; (4) green fluorescent protein; (5) green fluorescent protein; (6) beta-lactamase; (7) *Clostridium difficile* Toxin B; (8) *Clostridium difficile* Toxin A; (9) norovirus capsid (10) rotavirus capsid; (11) *Clostridium difficile* Toxin A; (12) *Plasmodium* membrane protein.

As shown in FIG. 3, subcellular fractionation results of transfectants expressing the single domain antibodies fused to the Sec-N22 leader sequence successfully secreted the recombinant polypeptide.

Figure 4:
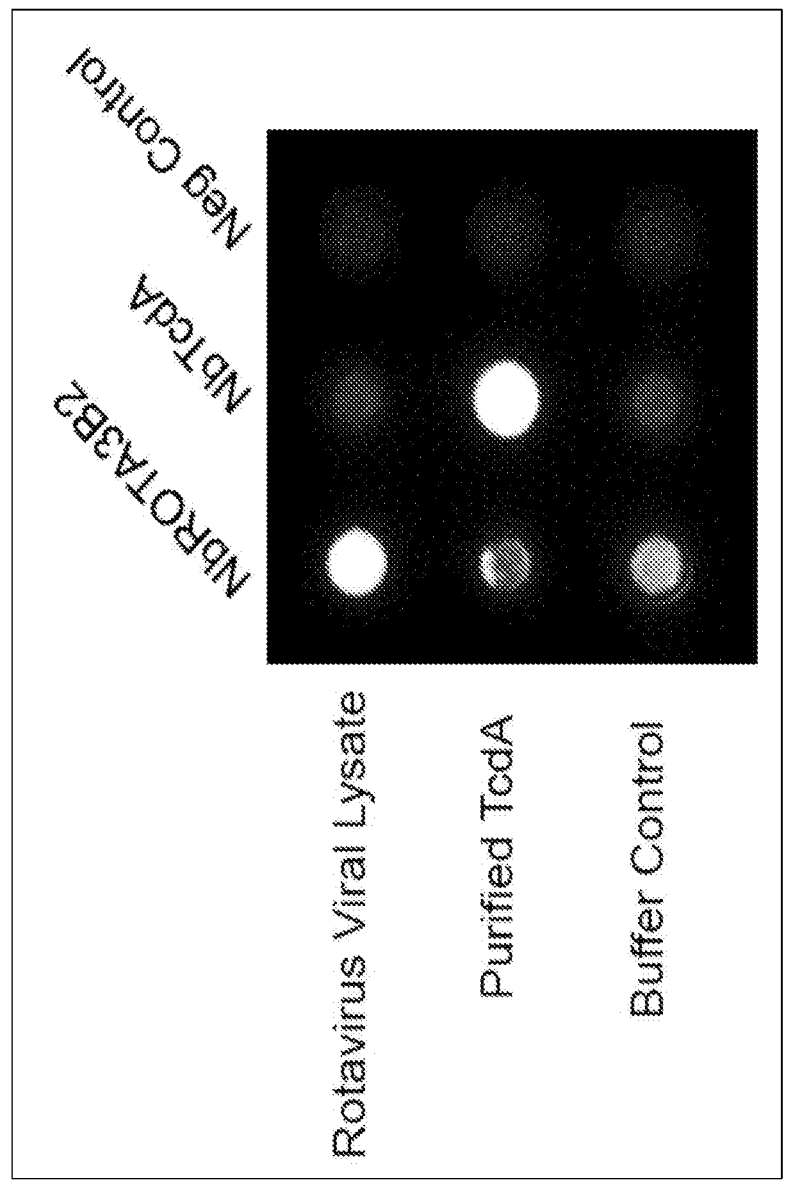
FIG. 4 shows a dot blot analysis of recombinant polypeptides comprising secreted single domain antibodies expressed from an *E. coli* Nissle 1917 comprising a heterologous nucleic acid encoding the native 42-amino acid Sec-N22 leader sequence from *E. coli* CsgA fused to either a single domain antibody specific for rotavirus capsid ("NbROTA3B2") or a single domain antibody specific for *Clostridium difficile* Toxin A ("NbTcdA"), which were reacted against rotavirus viral lysate, purified *C. difficile* Toxin A ("TcdA") or control buffer ("Buffer Control").
Figures 5A, 5B:
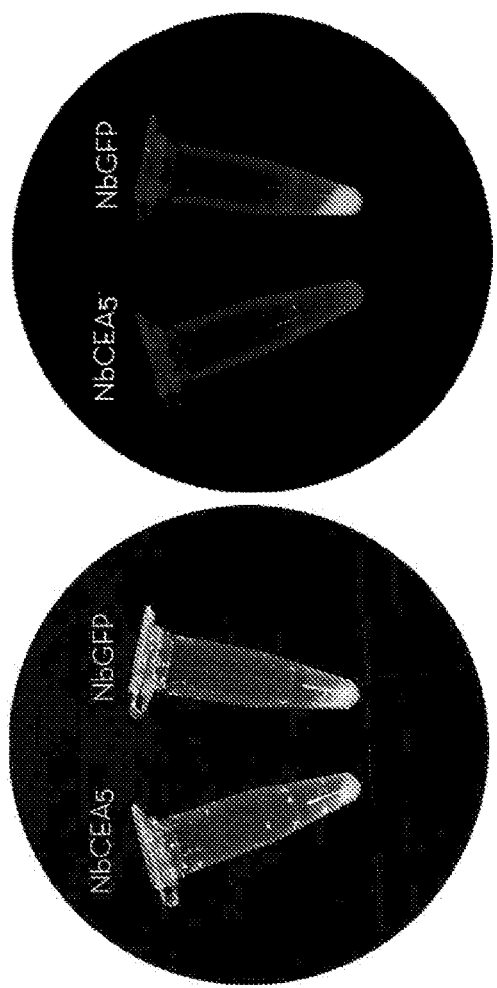
FIG. 5A shows a diagram of a secreted nanobody functionality experiment performed to detect the ability of secreted nanobodies against GFP to bind to GFP present in a cell lysate.
FIG. 5B shows photographs of reflected light microscopy imaging (left; "epi illumination") or fluorescence imaging (right; "GFP channel") of tubes comprising NiNTA beads bound to either secreted nanobodies targeting CEA5 ("NbCEA5") or secreted nanobodies targeting GFP ("NbGFP") and incubated with cell lysates comprising GFP.

To determine whether the secreted recombinant polypeptide was properly folded and capable of binding to the antigen of interest the following experiments were performed. First, dot blot analyses were performed with the secreted recombinant polypeptides comprising either a single domain antibody specific for rotavirus capsid or *Clostridium difficile* Toxin A. As shown in FIG. 4, the secreted recombinant polypeptide comprising a single domain antibody specific for rotavirus capsid was capable of binding to rotavirus viral lysate, and the secreted recombinant polypeptide comprising a single domain antibody specific for *C. difficile* Toxin A was capable of binding to purified *C. difficile* Toxin A ("TcdA"). Second, the ability of secreted nanobodies targeting green fluorescent protein (NbGFP), a product of the pBbA8c-NbGFP plasmid described above, to bind to GFP was assessed by immobilizing purified NbGFP onto NiNTA beads. Purified secreted nanobodies targeting CEA5 (NbCEA5) were immobilized onto NiNTA beads, and used as negative control. The beads were exposed to lysates from *E. coli* bacterial cells expressing green fluorescence protein, washed several times, and bead fluorescence detected (see diagram in FIG. 5A). As shown in FIG. 5B, the beads comprising secreted NbGFP bound to GFP as indicated by the detection of fluorescence, indicating that the secreted NbGFP retained functionality. No fluorescence was detected with the control beads comprising secreted NbCEA5. These experiments confirmed that the secreted recombinant polypeptides were properly folded and retained their functional properties.

Example 2: Generation of Engineered Bacteria Expressing Recombinant Polypeptides Comprising a SRP Pathway Signal Sequence, a CsgGE Export Signal Sequence and Single-Domain Antibodies Overexpression of secreted or outer membrane-targeted proteins can often lead to bottlenecks as the recombinant protein production levels begin to exceed the capacity of the periplasmic and/or outer membrane exporting systems. This can result in lowered yield of the recombinant protein as it begins to accumulate in the cell cytoplasm, often resulting in inclusion body formation that may be toxic to the bacterial cell. Although the *E. coli* Sec system is the dominant periplasmic export system for periplasmic as well as outer-membrane proteins, it requires that cytoplasmically-expressed protein unfolds as they are threaded through the Sec machinery. For proteins with structures that are extremely stable and recalcitrant to unfolding, this may pose a significant hurdle to efficient Sec-mediated transport.

An alternative transport system in bacterial cells, known as the signal recognition particle (SRP) pathway, allows for the co-translational translocation of proteins to the periplasm. In the SRP system, a specific N-terminal protein sequence is recognized by a complex which guides the nascent protein chain directly into the periplasm. Thus, protein folding occurs in the periplasm, avoiding folding-unfolding obstacles that may arise when Sec-mediated transportation is used. An SRP-mediated translocation strategy for single domain antibodies allows for protein folding to occur under the oxidizing conditions of the bacterial periplasm, thus minimizing protein misfolding. The expression of recombinant proteins having at least one stabilizing disulfide bond with an SRP pathway signal sequence may be particularly useful in facilitating proper protein folding. Therefore, engineered bacteria were developed by transfecting either a *E. coli* Nissle 1917 strain comprising a csgA knockout (PBP18) with pBbA8c plasmids comprising a heterologous nucleic acid encoding a single domain antibody specific for green fluorescent protein (GFP) fused to a SRP pathway signal sequence and the N22 leader sequence described in Example 1.

Briefly, a nucleic acid encoding a SRP pathway signal sequence from either CcmH (CcmH$_{SS}$), DsbA (DsbA$_{SS}$), FlgI (FlgI$_{SS}$), FocC (FocC$_{ss}$), NikA (NikA$_{SS}$), SfmC (SfmC$_{SS}$), TolB (TolB$_{SS}$), TorT (TorT$_{SS}$), or YraI (YraI$_{SS}$), was fused to a nucleic acid encoding the N22 leader sequence from *E. coli* strain MG1655 CsgA, a nucleic acid sequence encoding a single domain antibody specific for GFP, and a nucleic acid sequence encoding a poly-His polypeptide tag. DsbA, TolB, TorT, FocC, CcmH, NikA, or FlgI signal sequences were derived from *E. coli* Nissle. SfmC or TraI signal sequences were derived from *E. coli* K12 W3110. The constructs were cloned into the plasmid pBbA8C (Addgene plasmid #35272), whereby the nucleic acid is operably linked to an arabinose-inducible promoter. The constructs were transfected into *E. coli* Nissle bacterial cells.

Figure 6:
FIG. 6 shows a Western Blot of recombinant polypeptides comprising secreted single domain antibodies expressed rom an *E. coli* Nissle 1917 comprising a heterologous nucleic acid encoding the indicated SRP pathway signal sequence fused to the N22 leader sequence from *E. coli* CsgA fused to a single domain antibody specific for green fluorescent protein fused to a poly-His polypeptide tag. Secreted recombinant polypeptides were detected using horse-radish peroxidase-conjugated anti-His antibody.

As shown in FIG. 6, the various SRP pathway signal sequences used led to varying degrees of extracellular secretion of the recombinant polypeptide, demonstrating that SRP pathway signal sequences can be used for co-translational translocation to the periplasm and ultimate secretion of recombinant polypeptides, including single domain antibodies.

The three SRP pathway signal sequences that resulted in the highest level of secretion of the anti-GFP single domain antibody, FlgI$_{SS}$, SfmC$_{SS}$, and YraI$_{SS}$, were selected to be fused to single domain antibodies specific for other antigens.

Figure 7:
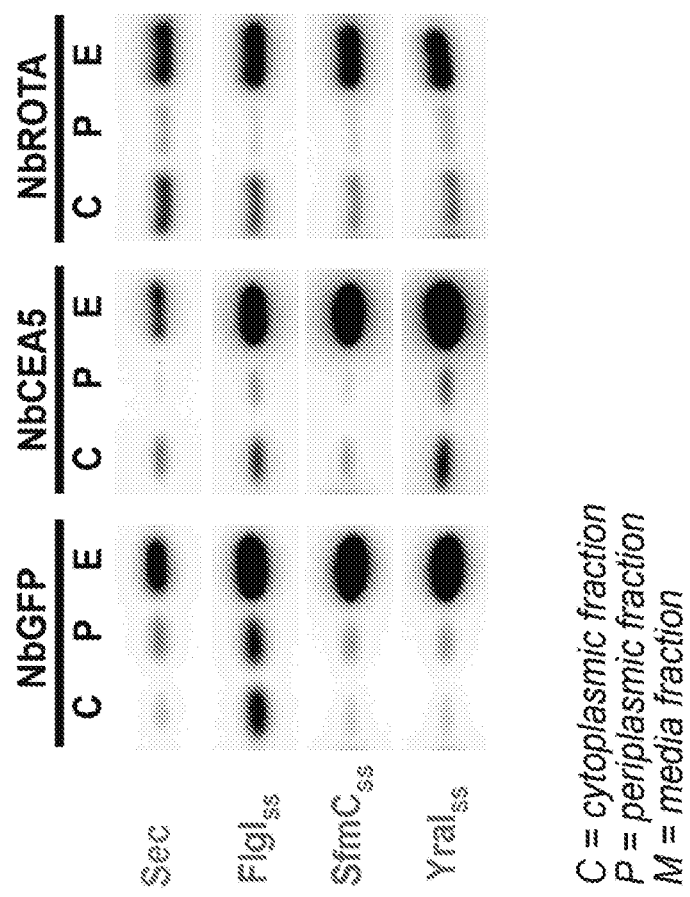
FIG. 7 shows a Western Blot of subcellular fractions derived from *E. coli* Nissle 1917 expressing a heterologous nucleic acid encoding the indicated SRP pathway signal sequence fused to the N22 leader sequence from *E. coli* CsgA fused to a single domain antibody specific for either (a) green fluorescent protein ("NbGFP"); (b) carcinogenic embryonic antigen ("NbCEA5"), and (c) rotavirus capsid (NbROTA); all fused to a poly-His polypeptide tag. The SRP pathway single sequences included the SRP pathway signal sequences from FlgI (FlgI$_{SS}$), SfmC (SfmC$_{SS}$), or YraI (YraI$_{SS}$), or a control which did not include an SRP pathway signal sequence ("Sec"). Secreted recombinant polypeptides were detected using horse-radish peroxidase-conjugated anti-His antibody.
Figure 8:
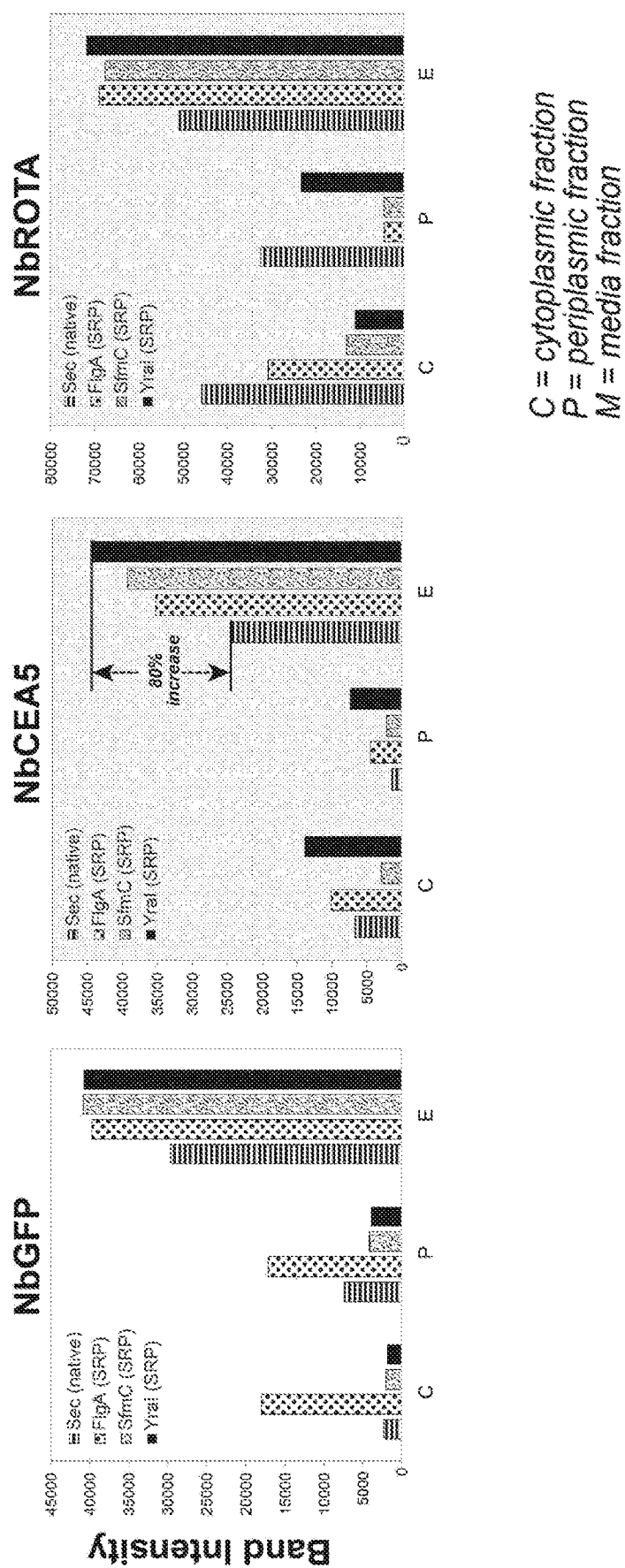
FIG. 8 shows a bar graph depicting the band intensity of the Western Blot of FIG. 7, assaying subcellular fractions derived from *E. coli* Nissle 1917 expressing a heterologous nucleic acid encoding the indicated SRP pathway signal sequence fused to the N22 leader sequence from *E. coli* CsgA fused to a single domain antibody specific for either (a) green fluorescent protein ("NbGFP"); (b) carcinogenic embryonic antigen ("NbCEA5"), and (c) rotavirus capsid (NbROTA); all fused to a poly-His polypeptide tag. C=cytoplasmic fraction; P=periplasmic fraction; E=extracellular fraction.

Briefly, a nucleic acid encoding a SRP pathway signal sequence from either FlgI (FlgI$_{SS}$), SfmC (SfmC$_{SS}$), or YraI (YraI$_{SS}$), was fused to a nucleic acid encoding the N22 leader sequence from *E. coli* strain MG1655 CsgA, a nucleic acid sequence encoding a single domain antibody specific for either GFP ("NbGFP"), carcinogenic embryonic antigen ("NBCEA5"), or rotavirus capsid ("NbROTA"), and a nucleic acid encoding a poly-His polypeptide tag. The constructs were cloned into the plasmid PBP18, whereby the nucleic acid is operably linked to an arabinose-inducible promoter. As shown in FIGS. 7 and 8, expression of these constructs in *E. coli* Nissle resulted in the export of the recombinant protein from the bacteria. The incorporation of an SRP pathway signal sequence significantly increased recombinant protein secretion confirms that artificially re-routing the VHH domains from the Sec pathway to the SRP pathway significantly increases the yield of extracellularly secreted VHH. For example, the secretion of the recombinant polypeptide comprising a single domain antibody specific for CEA fused to the SRP pathway signal sequence of YraI (YraI$_{SS}$) resulted in an 80% increase in recombinant polypeptide secretion, as compared to the secretion of recombinant polypeptide from bacteria transfected with a construct encoding the same single domain antibody specific for CEA in the absence of a SRP pathway signal sequence.

Figure 11A:
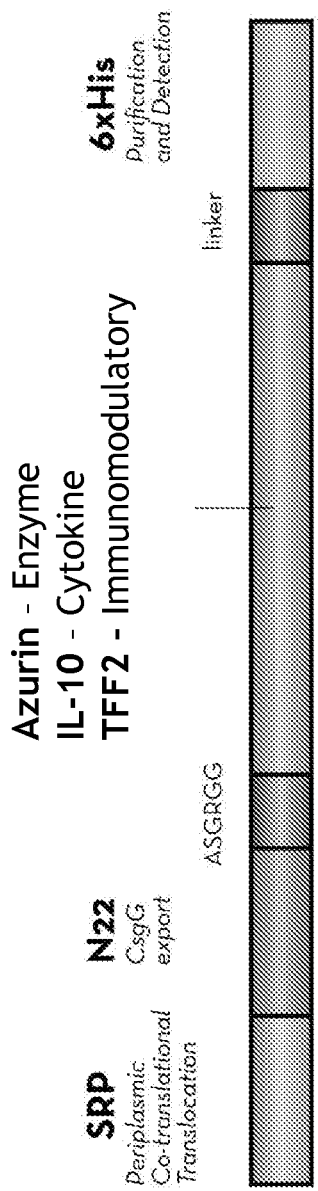
FIG. 11A depicts the structure of several recombinant proteins (azurin, IL-10 or TFF2) that were generated comprising the YraI$_{SS}$ SRP pathway signal sequence, the N22 leader sequence, and a poly-histidine tag.
Figure 11B:
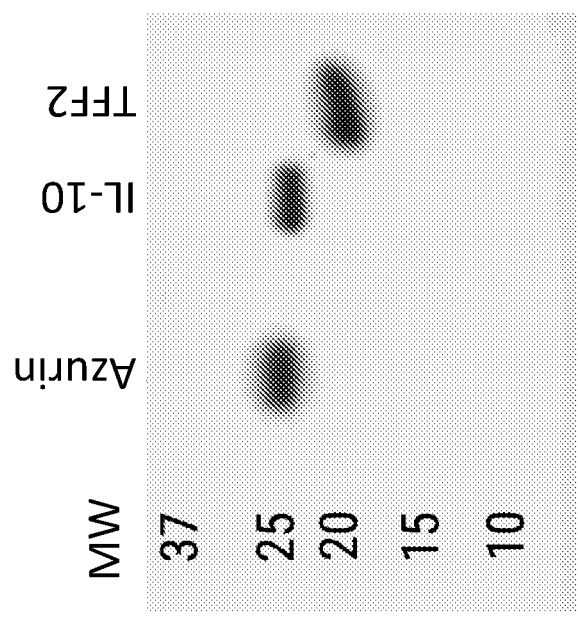
FIG. 11B shows a Western blot using anti-His antibody of the azurin, IL-10, and TFF2 that was secreted into cell culture media of bacterial cells transfected to express the recombinant proteins depicted in FIG. 11A.

To determine whether the SRP pathway secretion signal fused to the N22 leader sequence could be successfully used to induce the export of a variety of proteins in *E. coli*, the following experiment was performed. Constructs comprising a nucleic acid encoding the SRP pathway signal sequence from YraI (YraI$_{SS}$), fused to a nucleic acid encoding the N22 leader sequence from *E. coli* strain MG1655 CsgA, and either: a nucleic acid sequence encoding azurin, interleukin-10, or the immunomodulatory molecule TFF2, and a nucleic acid encoding a poly-His polypeptide tag (see diagram at FIG. 11A). The constructs were transfected into *E. coli* Nissle 1917 strain comprising a csgA knockout (PBP18). Transfected cells were cultured in 10 mL of LB media, and the secreted protein present in the culture media was purified using a Ni-NTA column. Secreted protein levels were assessed by performing Western blots using anti-His antibody. As shown in FIG. 11B, the cytokines IL-10 and TFF2, each comprising complex disulfide bonds, and the enzyme azurin, were successfully expressed and secreted using this expression system.

Example 3: Generation of pMUT1 Plasmids Comprising a Heterologous Nucleic Acid Encoding Red Fluorescent Protein (RFP) and Stable Transfection of *E. coli* Nissle 1917 in the Absence of a Selectable Marker Using a probiotic, for example the *E. coli* Nissle 1917 strain, for the in vivo production of a therapeutic protein (e.g., an antibody) in the absence of a selectable marker is highly desirable. For example, the use of an selectable marker, such as an antibiotic, for the maintenance of an expression plasmid in the probiotic could affect the bacterial flora of the subject to whom the probiotic and antibiotic is administered, which may lead to unknown consequences. To avoid the use of selectable markers, a heterologous nucleic acid encoding the therapeutic protein of interest can be integrated into the bacterial genome. However, the expression level of the therapeutic protein of interest may be reduced, as limited copy numbers of the heterologous nucleic acid may be incorporated into the bacterial genome. By contrast, the use of high-copy plasmid leads to 500-700 copies of the heterologous nucleic acid encoding the therapeutic protein of interest, vastly increasing the expression yield. A novel approach to expressing therapeutic proteins that does not require the use of a selectable marker has been developed allowing for high levels of expression of a therapeutic polypeptide of interest (e.g., a single domain antibody) in situ.

*E. coli* Nissle 1917 contains two cryptic high-copy plasmids, pMUT1 and pMUT2, specific to this *E. coli* strain. For example, *E. coli* Nissle 1917 strain validation by PCR uses primer probes that specifically detect the presence of these plasmids (Blum-Oehler et al. (2003)). Intriguingly, these plasmids are able to persist in *E. coli* Nissle 1917, including wild populations of the bacterial strain, suggesting the presence of a genetic mechanism responsible for plasmid retention (Kleta et al. (2014)). Surprisingly, here we demonstrate that heterologous nucleic acids can be incorporated into one of the plasmids, pMUT1, which can then be used to transform *E. coli* Nissle 1917 bacteria and remain stably integrated in the bacteria for a prolonged period of time without requiring the use of a selectable marker (e.g., an antibiotic).

Figure 9A:
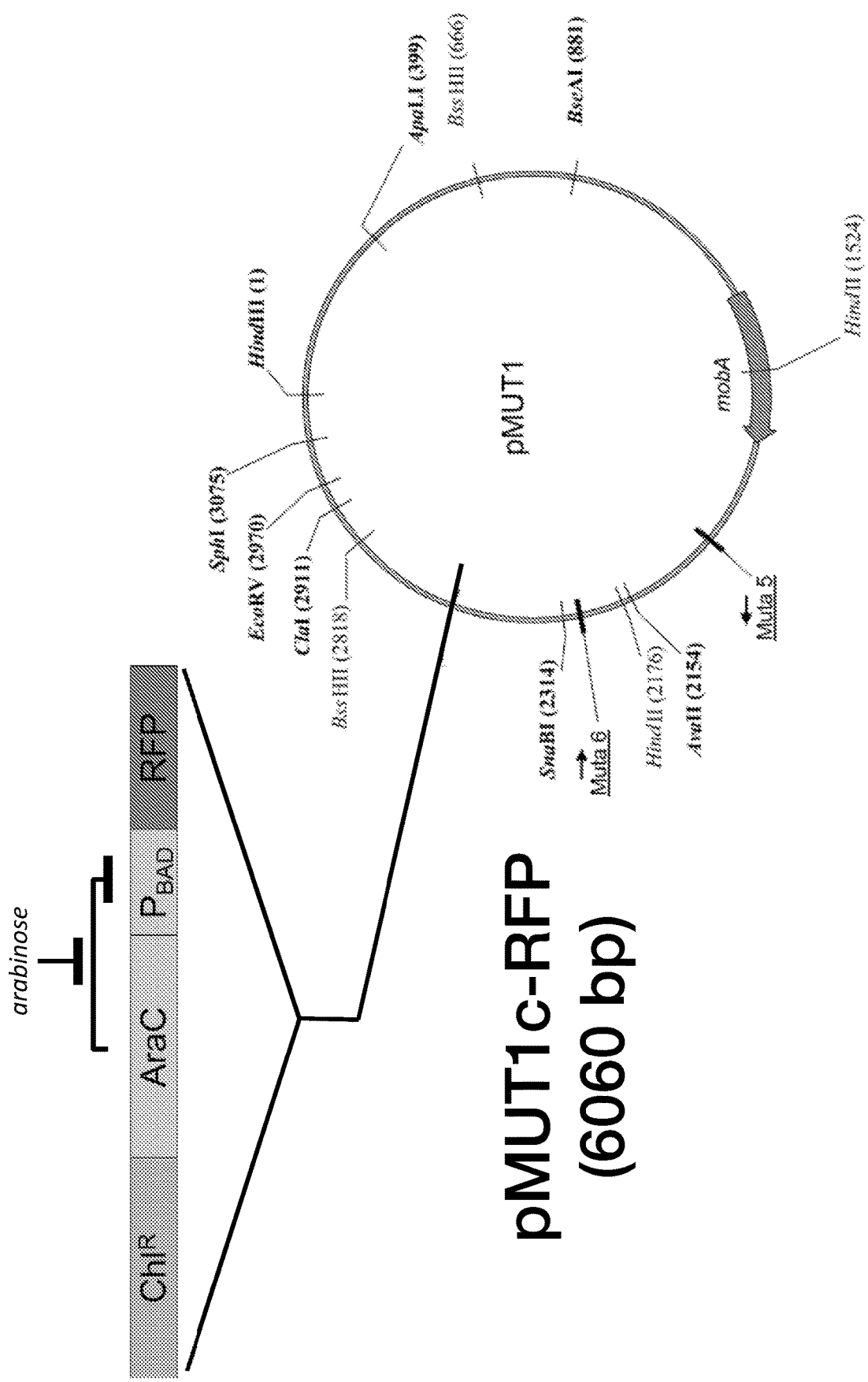
FIG. 9A is a schematic diagram showing the cloning of a gene cassette comprising red fluorescent protein (RFP) under the control of an arabinose promoter, and the chloramphenicol resistance gene, Chl$^R$, into the pMUT1 plasmid.
Figure 9B:
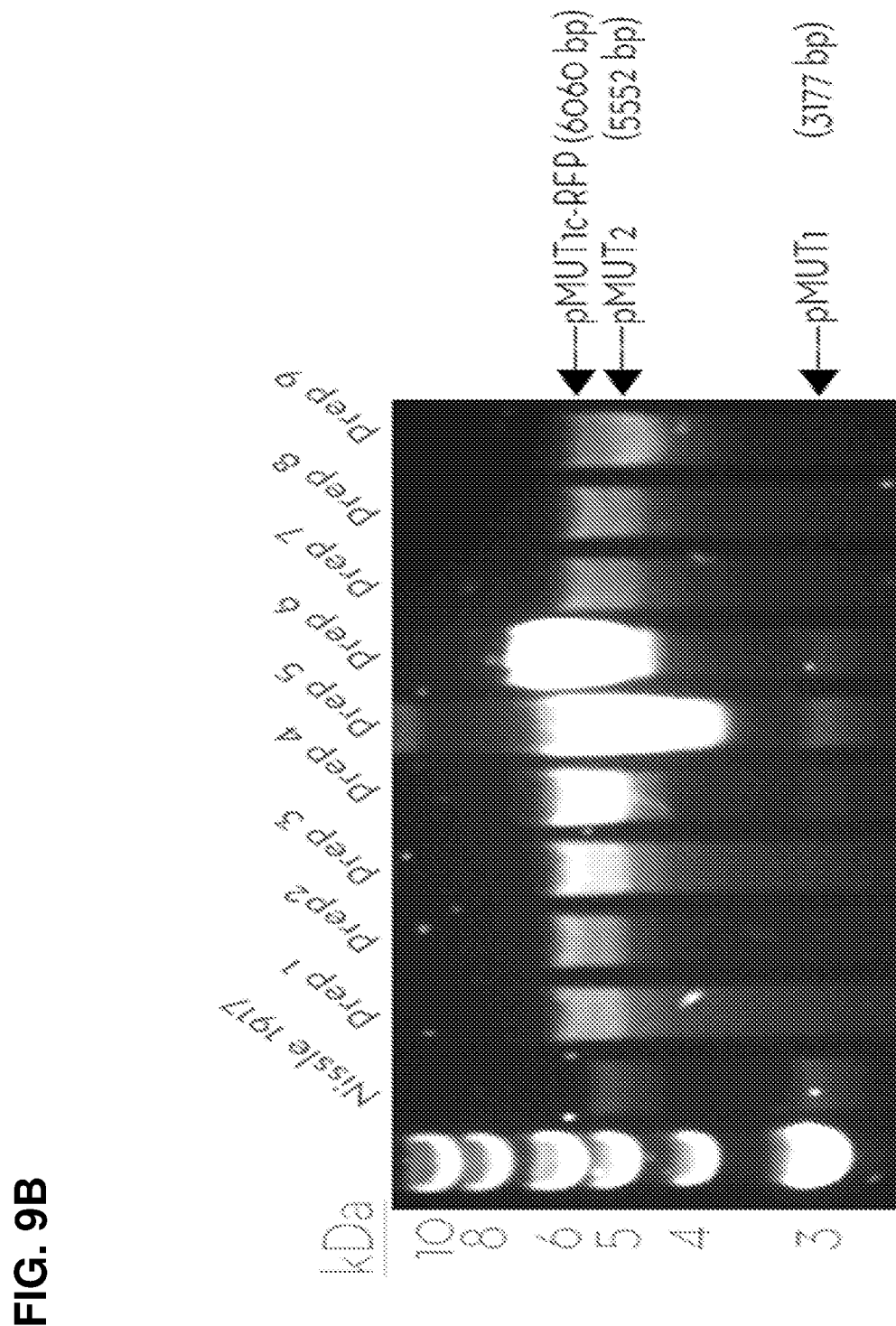
FIG. 9B shows an agarose gel electrophoresis of plasmid preparations from *E. coli* Nissle 1917 transfected with pMUT1 that has been engineered to comprise a gene encoding red fluorescent protein (RFP) (called pMUT1c-RFP herein). The location of endogenous pMUT1, endogenous pMUT2, and pMUT1c-RFP is indicated. Preparations 2, 7, 8 and 9 show the stable integration of the engineered pMUT1c-RFP in *E. coli* Nissle 1917 bacteria.

Briefly, a heterologous nucleic acid encoding red fluorescent protein was cloned into pMUT1 to create the plasmid pMUT1c-RFP (see FIG. 9A). The heterologous nucleic acid comprises a chloramphenicol resistance gene that can be used to select for bacteria transfected with the plasmid. *E. coli* Nissle 1917 was transfected with the pMUT1c-RFP. The transfected bacteria were initially plated onto Luria broth (LB) agar plates with chloramphenicol for several rounds to replace the endogenous pMUT1 plasmid with the pMUT1c-RFP plasmid. As shown in FIG. 9B, the engineered plasmid pMUT1c-RFP was integrated into Nissle in place of the native pMUT1 plasmid (see Preps 2, 7, 8, and 9).

Figure 10:
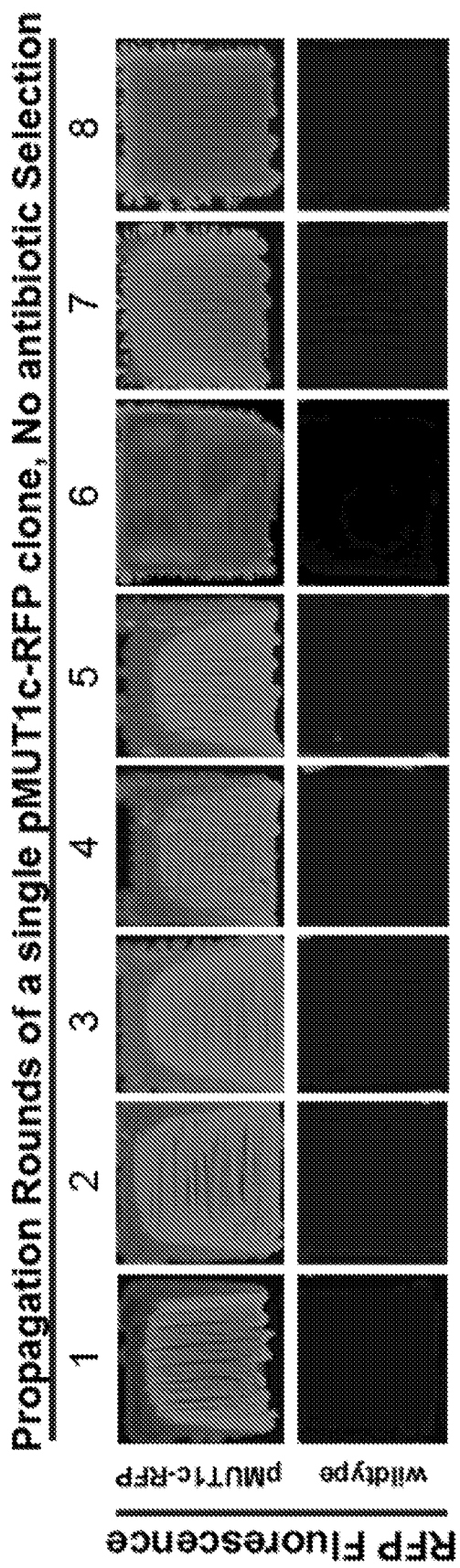
FIG. 10 shows fluorescence imaging of *E. coli* Nissle 1917 untransfected clones ("wildtype") and clones transfected with pMUT1c-RFP ("pMUT1c-RFP") and grown in the absence of a selectable marker after several propagation cycles.

To determine whether the transformed bacteria were able to maintain the engineered plasmid, as evidenced by RFP expression, for several propagation cycles, transformed cells were grown in the absence of a selectable marker by streaking the cells onto an LB plate (without antibiotic) and incubating the plate at 37° C. for 24-48 hours. RFP protein expression was assessed to determine the maintenance of the pMUT1c-RFP plasmid in transformants. As shown in FIG. 10, transformants expressed RFP without the need for any antibiotic selection after 14 propagation cycles.

REFERENCES

1. Blum-Oehler et al. (2003) *Research in Microbiology*, 154(1): 59-66.
2. Chapman et al. (2002). *Science* 295(5556): 851-855.
3. de Marco (2011). *Microbial Cell Factories*, 10(1), 44.
4. Ditlev et al. (2014). *PLoS ONE*, 9(1): 1-10.
5. Doshi et al. *Scientific Reports* 4, 6760.
6. Dueholm et al. (2012) *PLoS ONE* 7(12).
7. Goyal et al. (2014) *Nature* 516(7530): 250-3.
8. Hussack et al. (2011) *Journal of Biological Chemistry* 286(11): 8961-8976.
9. Kleta et al. (2014) *Infection and Immunity* 82(5): 1801-1812.
10. Koromyslova and Hansman (2015) *Journal of Virology*, 89(5): 2718-30.
11. Nenninger et al. (2011) *Molecular Microbiology* 81(2): 486-499.
12. Rothbauer et al. (2006) *Nature Methods* 3(11): 887-9.
13. Saerens et al. (2005) *Journal of Molecular Biology* 352(3): 597-607.
14. Vaneycken et al. (2010) *Journal of Nuclear Medicine* 51(7): 1099-106.
15. Vega et al. (2013) *PLoS Pathogens* 9(5).
16. Yang et al. (2014) *Journal of Infectious Diseases* 210(6): 964-972.

The invention claimed is:

1. An engineered bacterium comprising a heterologous nucleic acid, wherein the heterologous nucleic acid comprises
a nucleic acid sequence encoding a signal recognition particle (SRP) pathway signal sequence,
a nucleic acid sequence encoding a CsgGE export signal sequence, and
a nucleic acid sequence encoding a therapeutic polypeptide.

2. The engineered bacterium of claim 1, wherein the CsgGE export signal sequence is an *E. coli* CsgGE export signal sequence.

3. The engineered bacterium of claim 1, wherein the SRP pathway signal sequence comprises a signal sequence selected from the group consisting of a CcmH signal sequence, a DsbA signal sequence, a FlgI signal sequence, a SfmC signal sequence, a FocC signal sequence, a NikA signal sequence, a TolB signal sequence, a TorT signal sequence, and a YraI signal sequence.

4. The engineered bacterium of claim 1, wherein the therapeutic polypeptide is selected from the group consisting of an antibody, an antibody fragment, an enzyme, a fusion protein, a hormone, an antigen, a thrombolytic agent, a cytokine, an immunotoxin, and a growth factor.

5. The engineered bacterium of claim 4, wherein the antibody fragment is a single domain antibody specific for an antigen selected from the group consisting of: carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, and *Plasmodium* membrane protein.

6. The engineered bacterium of claim 1, wherein the nucleic acid sequence encoding the SRP pathway signal sequence and the nucleic acid sequence encoding the CsgGE export signal sequence are located N-terminal to the nucleic acid sequence encoding the therapeutic polypeptide.

7. The engineered bacterium of claim 1, wherein the heterologous nucleic acid further comprises a nucleic acid sequence encoding a polypeptide tag selected from the group consisting of a poly-histidine tag, a myc tag, a FLAG tag, a hemagglutinin (HA) tag, and a V5 tag.

8. The engineered bacterium of claim 1, wherein the engineered bacterium is of the species *Escherichia coli*.

9. The engineered bacterium of claim 1, wherein the engineered bacterium further comprises a heterologous csgE gene, a heterologous csgG gene, a heterologous ffh gene, a heterologous ftsY gene, a heterologous ffs gene, a native csgE gene, a native csgG gene, a native ffh gene, a native ftsY gene, or a native ffs gene.

10. The engineered bacterium of claim 1, wherein the heterologous nucleic acid is operably linked to a constitutive or inducible promoter.

11. A pharmaceutical composition comprising the engineered bacterium of claim 1, and a pharmaceutically acceptable excipient.

12. A method of producing a recombinant polypeptide, comprising
culturing the engineered bacterium of claim 1 under conditions suitable for expression and export of the recombinant polypeptide from the engineered bacterium,
wherein the recombinant polypeptide comprises the CsgGE export signal sequence and the therapeutic polypeptide.

13. The method of claim 12, further comprising collecting the recombinant polypeptide from cell culture medium comprising the engineered bacterium.

14. The method of claim 13, wherein the recombinant polypeptide is collected from a supernatant of the cell culture medium.

15. A method for treating a gastrointestinal disease or disorder in a subject, the method comprising
administering the engineered bacterium of claim 1 to the subject,
wherein the engineered bacterium expresses and exports a recombinant polypeptide;
wherein the recombinant polypeptide comprises the CsgGE export signal sequence and a therapeutic polypeptide;
wherein the therapeutic polypeptide is therapeutic for a gastrointestinal disease or disorder selected from the group consisting of inflammatory bowel disease, Crohn's disease, ulcerative colitis, colorectal cancer, ulcer, malabsorption, short-gut syndrome, cul-de-sac syndrome, celiac sprue, tropical sprue, hypogammaglobulinemic sprue, enteritis, short bowel syndrome, and gastrointestinal cancer;

thereby treating the gastrointestinal disease or disorder in the subject.

16. A method for treating a systemic disease or disorder in a subject, the method comprising administering the engineered bacterium of claim 1 to the subject, wherein the engineered bacterium expresses and exports a recombinant polypeptide;

wherein the recombinant polypeptide comprises the CsgGE export signal sequence and a therapeutic polypeptide;

wherein the therapeutic polypeptide is therapeutic for a systemic disease or disorder selected from the group consisting of an allergy, an autoimmune disease, asthma, rheumatoid arthritis, diabetes, lupus, a viral infection, a bacterial infection, a protozoal infection, a fungal infection, cancer, multiple sclerosis, a congenital genetic disorder, a tissue or organ trauma, toxin ingestion, heavy metal poisoning, aging, and a metabolic disorder;

thereby treating the systemic disease or disorder in the subject.

17. A vector comprising a heterologous nucleic acid, wherein the heterologous nucleic acid comprises a nucleic acid sequence encoding a signal recognition particle (SRP) pathway signal sequence, a nucleic acid sequence encoding a CsgGE export signal sequence, and a nucleic acid sequence encoding a therapeutic polypeptide.

18. The vector of claim 17, further comprising a nucleic acid encoding a detectable protein selected from a fluorescent protein and a near infrared fluorescent protein.

19. The method of claim 15, wherein the therapeutic polypeptide is selected from the group consisting of an antibody, an antibody fragment, an enzyme, a fusion protein, a hormone, an antigen, a thrombolytic agent, a cytokine, an immunotoxin, and a growth factor.

20. The method of claim 19, wherein the therapeutic polypeptide is an antibody fragment; and the antibody fragment is a single domain antibody specific for an antigen selected from the group consisting of: carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, and *Plasmodium* membrane protein.

21. The method of claim 16, wherein the therapeutic polypeptide is selected from the group consisting of an antibody, an antibody fragment, an enzyme, a fusion protein, a hormone, an antigen, a thrombolytic agent, a cytokine, an immunotoxin, and a growth factor.

22. The method of claim 21, wherein the therapeutic polypeptide is an antibody fragment; and the antibody fragment is a single domain antibody specific for an antigen selected from the group consisting of: carcinogenic embryonic antigen (CEA), glucose transporter 1 (GLUT1), green fluorescent protein (GFP), beta-lactamase, *Clostridium difficile* Toxin A, *Clostridium difficile* Toxin B, botulinum toxin (BoTox), cholera toxin (CTX), norovirus capsid protein, rotavirus capsid protein, and *Plasmodium* membrane protein.

* * * * *